United States Patent
Hahn et al.

(10) Patent No.: US 11,944,692 B2
(45) Date of Patent: Apr. 2, 2024

(54) THERMOACTIVE DENTAL COMPOSITE COMPOSITION

(71) Applicant: VOCO GMBH, Cuxhaven (DE)

(72) Inventors: Christoph Hahn, Cuxhaven (DE);
Gerrit Lübbe, Cuxhaven (DE);
Reinhard Maletz, Cuxhaven (DE);
Manfred Thomas Plaumann, Cuxhaven (DE)

(73) Assignee: VOCO GMBH, Cuxhaven (DE)

( * ) Notice: Subject to any disclaimer, the term of this patent is extended or adjusted under 35 U.S.C. 154(b) by 514 days.

(21) Appl. No.: 17/252,588

(22) PCT Filed: Jun. 18, 2019

(86) PCT No.: PCT/EP2019/066027
§ 371 (c)(1),
(2) Date: Dec. 15, 2020

(87) PCT Pub. No.: WO2019/243339
PCT Pub. Date: Dec. 26, 2019

(65) Prior Publication Data
US 2021/0267849 A1    Sep. 2, 2021

(30) Foreign Application Priority Data
Jun. 19, 2018  (DE) ............ 10 2018 114 690.6

(51) Int. Cl.
*A61K 6/887* (2020.01)
*A61K 6/64* (2020.01)
*A61K 6/77* (2020.01)
(52) U.S. Cl.
CPC .......... *A61K 6/887* (2020.01); *A61K 6/64* (2020.01); *A61K 6/77* (2020.01)

(58) Field of Classification Search
CPC .................................................. A61K 6/15
See application file for complete search history.

(56) References Cited

U.S. PATENT DOCUMENTS 4,002,669 A    1/1977  Gross
4,131,729 A    12/1978 Schmitt
(Continued)

FOREIGN PATENT DOCUMENTS

CA    1109597    9/1981
CA    2256191    7/1999
(Continued)

OTHER PUBLICATIONS

English language machine translation of Sato et al. (JP 2001-139411). (Year: 2001).*
(Continued)

*Primary Examiner* — Michael F Pepitone
(74) *Attorney, Agent, or Firm* — DUANE MORRIS LLP; Gregory M. Lefkowitz; Brandon A. Chan

(57) ABSTRACT

The present invention relates to dental, light-curable, one-component composite compositions comprising (A) monomers, (B) fillers, and (C) initiators, the viscosity $\eta_{20}$ of which at 20° C. is greater than 400 Pa*s, preferably greater than 800 Pa*s and more preferably greater than 1200 Pa*s, and the viscosity $\eta_{50}$ of which at 50° C. is less than 150 Pa*s, preferably less than 120 Pa*s and more preferably less than 90 Pa*s, and wherein the quotient $\eta_{50}/\eta_{20}$ of the viscosity of the composite composition at 50° C. and the viscosity of the composite composition at 20° C. is less than 0.125, preferably less than 0.1. The invention is preferably directed to dental composite compositions selected from the group consisting of dental filling materials, lining materials, luting materials and fissure sealants.

27 Claims, 1 Drawing Sheet

(56) References Cited

U.S. PATENT DOCUMENTS

| | | | |
|---|---|---|---|
| 4,298,738 A | 11/1981 | Lechtken |
| 4,323,348 A | 4/1982 | Schmitz-Josten |
| 4,323,696 A | 4/1982 | Schmitz-Josten |
| 4,447,520 A | 5/1984 | Henne |
| 4,522,693 A | 6/1985 | Henne |
| 4,737,593 A | 4/1988 | Ellrich |
| 4,744,827 A | 5/1988 | Winkel |
| 4,744,828 A | 5/1988 | Winkel |
| 4,772,530 A | 9/1988 | Gottschalk |
| 4,868,091 A | 9/1989 | Boettcher |
| 4,874,450 A | 10/1989 | Gottschalk |
| 4,952,614 A | 8/1990 | Reiners |
| 4,954,414 A | 9/1990 | Adair |
| 5,055,372 A | 10/1991 | Shanklin |
| 5,057,393 A | 10/1991 | Shanklin |
| 5,063,257 A | 11/1991 | Akahane |
| 5,100,929 A | 3/1992 | Jochum |
| 5,319,054 A | 6/1994 | Slack |
| 5,399,770 A | 3/1995 | Leppard |
| 5,440,003 A | 8/1995 | Slack |
| 5,472,991 A | 12/1995 | Schmitt |
| 5,761,169 A | 6/1998 | Mine |
| 5,847,025 A | 12/1998 | Moszner |
| 6,020,528 A | 2/2000 | Leppard |
| 6,191,191 B1 | 2/2001 | Harada |
| 6,236,020 B1 | 5/2001 | Friedman |
| 6,312,254 B1 | 11/2001 | Friedman |
| 6,320,162 B1 | 11/2001 | Friedman |
| 6,616,448 B2 | 9/2003 | Friedman |
| 7,015,423 B2 | 3/2006 | Friedman |
| 7,081,485 B2 | 7/2006 | Suh |
| 7,097,452 B2 | 8/2006 | Friedman |
| 7,148,382 B2 | 12/2006 | Wolf |
| 2002/0035169 A1 | 3/2002 | Nakatsuka |
| 2003/0162863 A1 | 8/2003 | Satoh |
| 2006/0020590 A1 | 9/2006 | Shooshtari |
| 2007/0002722 A1 | 2/2007 | Moszner |
| 2008/0277814 A1 | 11/2008 | Moszner |
| 2009/0036565 A1 | 2/2009 | Utterodt |
| 2009/0047622 A1 | 2/2009 | Leiner |
| 2010/0041789 A1 | 2/2010 | Neffgen |
| 2011/0046261 A1* | 2/2011 | Kuboe .................. A61K 6/887 523/115 |
| 2012/0083550 A1 | 4/2012 | Bloemker |
| 2012/0196952 A1* | 8/2012 | Suzuki .................. A61K 6/887 523/105 |
| 2015/0342841 A1 | 12/2015 | Lübbe |
| 2016/0113846 A1 | 4/2016 | Willner |
| 2021/0267849 A1 | 9/2021 | Hahn et al. |

FOREIGN PATENT DOCUMENTS

| | | |
|---|---|---|
| DE | 2200021 | 7/1973 |
| DE | 4416857 | 6/1995 |
| DE | 19860364 | 6/2000 |
| DE | 60116142 | 7/2006 |
| DE | 102005021332 | 11/2006 |
| DE | 102006019092 | 3/2007 |
| DE | 102006050153 | 5/2008 |
| DE | 102007034457 | 1/2009 |
| EP | 0007508 | 2/1980 |
| EP | 0106176 | 4/1984 |
| EP | 0173567 | 3/1986 |
| EP | 1151728 | 11/2001 |
| EP | 1563821 | 8/2005 |
| EP | 1685182 | 8/2006 |
| EP | 1874847 | 1/2008 |
| EP | 2016962 | 1/2009 |
| JP | 2001139411 A * | 5/2001 |
| WO | 200144873 | 6/2001 |
| WO | 2002085974 | 10/2002 |
| WO | 2005011621 | 2/2005 |
| WO | 2013041723 | 3/2013 |
| WO | 2013053693 | 4/2013 |
| WO | 2018071920 | 4/2018 |

OTHER PUBLICATIONS

Blalock, J.S., et al., "Effect of temperature on unpolymerized composite resin film thickness," The Journal of Prosthetic Dentistry, Dec. 2006, 96(6):424-432.

Lohbauer U. et al., "The effect of resin composite pre-heating on monomer conversion and polymerization shrinkage", Academy of Dental Materials, Elsevier, Apr. 2009, vol. 25, Issue 4, 514-519.

J. Friedman, Thermally assisted polymerization of composite resins, Contemp. Esthet. Restor. Pract., 7, 46, 2003 and H. E. Strassler, R. D. Trushkowsky, Predictable restoration of Class 2 preparations with composite resin, Dent. Today, 23, 93-99, 2004.

M. Trujillo, S. M. Newmann, J. W. Stansburry, Use of near-IR to monitor the influence of external heating on dental composite photopolymerization, Dent. Mater. 20, 766-777, 2004.

F. C. Calheiros, M. Daronch, F. A. Rueggeberg, R. R. Braga, Effect of temperature on composite polymerization stress and degree of conversion, Dent. Mater. 30, 613-618, 2014.

N. R. Froes-Salgado, L. M. Silva, Y. Kawano, C. Francci, A. Reis, A. D. Loguercio, Composite pre-heating: Effects on marginal adaptation, degree of conversion and mechanical properties, Dent. Mater. 26, 908-915, 2010.

J. da Costa et al., Effect of heat on the flow of commercial composites, Am. J. Dent. 2009, 22 (2), 92-96.

M. Goulart et al., Effect of pre-heating composites on film thickness, Journal of Research in Dentistry, 2013, 1 (4), 274-280.

S. Deb et al., Pre-warming of dental composites, Dental Materials 2011, 27, e51-e59.

S. Lucey et al., Effect of pre-heating on the viscosity and microhardness of a resin composite, Journal of Oral Rehabilitation 2010, 37, 278-282.

H. Stemmer, 2001, Friedrich-Schiller University of Jena, entitled "Homogene Katalyse in überkritischem Kohlendioxid: Analogien und Unterschiede zu konventionellen Lösungsmitteln" [Homogeneous Catalysis in Supercritical Carbon Dioxide: Analogies and Differences from Conventional Solvents.

N. Moszner et al. "Synthesis and polymerisation of new multifunctional urethane methacrylates", Die Angewandte Makromolekulare Chemie 265 (1999), 31-35.

N. Moszner et al. "A partially aromatic urethane dimethacrylate as a new substitute for bis-GMA in restorative composites", Dental Materials, 24 2008, 694-699.

Chemische Identität einzelner Partikel [Chemical Identity of Individual Particles] by Deborah Huck Jones and Renate Hessemann in "Nachrichten aus der Chemie", vol. 62, Sep. 2014, pp. 886 and 887.

J. P. Fouassier, Photoinitiation, Photopolymerization and Photocuring, Hanser Publishers, Munich, Vienna, New York 1995, and in J. F. Rabek (ed.), Radiation Curing in Polymer Science and Technology, vol. II, Elsevier Applied Science, London, New York 1993.

H. E. Strassler, R. D. Trushkowsky, Predictable restoration of Class 2 preparations with composite resin, Dent. Today, 23, 93-99, 2004.

Tauböck Tobias T., Tarle Zrinka, Marovic Danijela, Attin Thomas: "Pre-heating of high-viscosity bulk-fill resin composites: Effects on shrinkage force and monomer conversion", Journal of Dentistry, vol. 43, No. 11, Nov. 1, 2015 (Nov. 1, 2015), Amsterdam, NL , pp. 1358-1364, XP055864856, ISSN: 0300-5712, DOI: 10.1016/j.jdent. 2015.07.014.

* cited by examiner

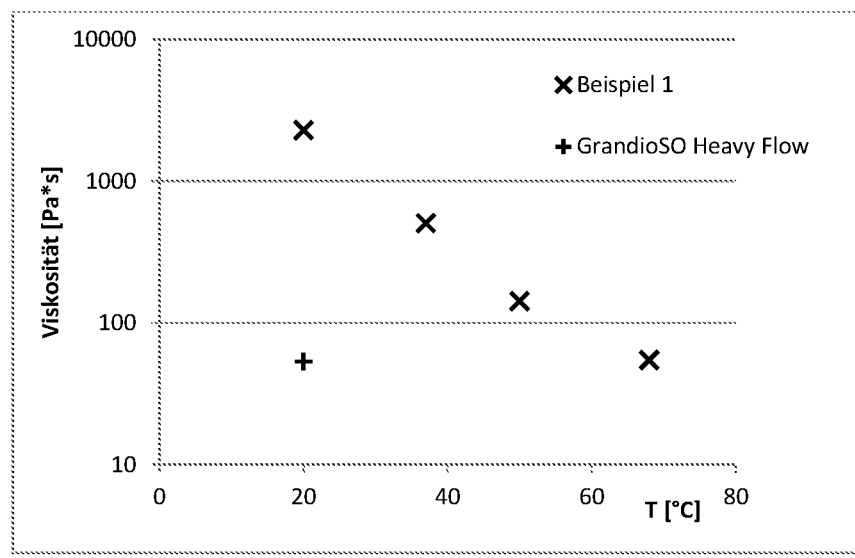

THERMOACTIVE DENTAL COMPOSITE COMPOSITION

CROSS-REFERENCE TO RELATED APPLICATIONS

This application is a § 371 national stage entry of International Application No. PCT/EP2019/066027, filed on Jun. 18, 2019, which claims priority to German Patent Application No. 10 2018 114690.6, filed on Jun. 19, 2018, the entire contents of which are incorporated herein by reference.

The present invention relates to dental, light-curable, one-component composite compositions comprising (A) monomers, (B) fillers, and (C) initiators, the viscosity $\eta_{20}$ of which at 20° C. is greater than 400 Pa*s, preferably greater than 800 Pa*s and more preferably greater than 1200 Pa*s, and the viscosity $\eta_{50}$ of which at 50° C. is less than 150 Pa*s, preferably less than 120 Pa*s and more preferably less than 90 Pa*s, and wherein the quotient $\eta_{50}/\eta_{20}$ of the viscosity of the composite composition at 50° C. and the viscosity of the composite composition at 20° C. is less than 0.125, preferably less than 0.1.

The invention is preferably directed to dental composite compositions selected from the group consisting of dental filling materials, lining materials, luting materials and fissure sealants. The invention likewise relates to cured composite compositions that are obtained by light curing of the dental, light-curable, one-component composite compositions of the invention. A further aspect of the invention is dental, light-curable, one-component composite compositions for use in a method of dental treatment, preferably as a dental material preheated to 40° C. to 80° C. for filling of teeth and/or for luting of crowns, inlays, onlays and veneers and/or for sealing of fissures. The invention additionally relates to the use of the dental, light-curable, one-component composite composition for production of a dental product, preferably preheated to 40° C. to 80° C. Moreover, the invention relates to a method of preparing for a dental treatment. In a particular embodiment, aspects of the invention are a specific device for application of the composite composition of the invention and a method of producing the composite composition. The invention is defined in the appended claims.

Dental composite materials are composites composed of a resin and inorganic filler. Conventionally, they thus consist fundamentally of various units: a polymerizable organic matrix, filler particles and (typically) an agent that ensures the bond between the (cured) polymer and the filler particles. Dental composite materials are used in the form of curable compositions that are polymerized after application thereof.

Dental restorative materials are a specific form of composite materials because they are subjected to the highest demands due to their extreme physical and chemical stress in the exceedingly hostile environment of the mouth. Due to their extreme requirements, these materials often serve as a basis for the development of non-dental composites, or as a model for use in the non-dental field.

STATE OF THE ART

Dental restorative composite materials have been used for almost 60 years for uses including filling and lining treatment, as luting materials and as fissure sealants. After being introduced into the cavity, or after application to the surface of the tooth, dental composites cure chemically and/or under supply of external energy in a polymerization reaction.

The organic polymerizable component of the dental composite material is generally crosslinked in a free-radical reaction and correspondingly contains ethylenically unsaturated functional groups. The monomers and oligomers include the mono-, di- and/or polyacrylates and/or methacrylates, for example the diglycidyl methacrylate of bisphenol A ("bis-GMA", 2,2-bis[4-(2-hydroxy-3-methacryloyloxypropyloxy)phenyl]propane) and the diurethane di(meth)acrylate formed from 2,2,4-trimethylhexamethylene diisocyanate and 2-hydroxyethyl (meth)acrylate (UDMA). Where (meth)acrylates are mentioned hereinafter, this always also means the analogous acrylates in the context of this invention. Commercially available standard mixtures contain bis-GMA, UDMA and triethylene glycol dimethacrylate for lowering the viscosity.

In order to be able to free-radically cure the resin mixture, an initiator system which is added to the compound triggers the free-radical polymerization, for example after irradiation. A typical system that initiates the free-radical polymerization of the (meth)acrylates consists of a photoinitiator (ketone) and an accelerator (amine). The ketone used may typically be camphorquinone, and the amine para-N,N-dimethylaminobenzoic acid. Further photoactive constituents may be added to the mixture. Other known photoinitiators that are used individually or in combination with the camphorquinone/amine system are phosphine oxides, especially phenylbis(2,4,6-trimethylbenzoyl)phosphine oxide and/or 2,4,6-trimethylbenzoyldiphenylphosphine oxide. Likewise known is the use of borate salts as photoinitiators. Further photoinitiators may be selected from the group consisting of benzoin alkyl ethers, benzoin alkyl esters, benzil monoketals, benzophenones, acetophenones, ketals, thioxanthones and titanocenes.

If the composition is exposed to a suitable radiation source at 470 nm, the composite material undergoes photochemical crosslinking.

The inorganic fillers in the dental composite material generally consist of quartz, borosilicate glass, lithium aluminium silicate, barium aluminium silicate, strontium/barium glass, zinc glass, zirconium silicate, fumed or colloidal silica, and nanoscale metal oxides.

The bond of the inorganic filler bodies to the organic resin matrix is generally ensured by the use of coupling reagents and adhesion promoters. This method step is essential for the later suitability of the composite compound as dental material. This involves treating the filler with a silane, usually in the presence of weak acids, before it is blended with the liquid resin component.

Further constituents of a composite material include dyes, pigments, stabilizers, inhibitors, co-initiators, wetting agents, etc.

The characteristics of the resulting dental composite material are determined primarily by the inorganic phase. While the Young's modulus for an unfilled resin system based on bis-GMA is 2.8 GPa, the enamel has a value of 83 GPa and the dentine a value of 19 GPa. By adding a conventional silylated filler to the bis-GMA resin, the value of 2.8 GPa can be distinctly improved. If the filler is added to the resin in a volume ratio of 1:1.25, the Young's modulus can be raised to a value of 18 GPa. For a ratio of 1:1, a value of 30 GPa can be achieved.

For a given resin composition, the type of filler, amount and particle distribution determine the mechanical, aesthetic and rheological characteristics of a dental filling composite such as surface hardness, abrasion resistance, wear resistance, compressive strength, tensile strength, polymerization shrinkage, fracture resistance and thermal cycling stability, and also polishability, gloss, opacity, translucence and colour stability, and also flow characteristics, malleability and modellability. The rule of thumb is that: the higher the loading of the liquid resin with silanized filler, the better the mechanical, physical and chemical properties of the cured moulding material.

Against the background of the major importance of the inorganic phase for the properties of dental composite materials, it is also possible to comprehend the traditional classification of dental composite materials in three different basic classes.

A macro-filled composite material is a composition with a high filler level (up to 87% by weight) of relatively large particles (1-100 μm). While the filler used was previously glass powder having an average particle size of 30-50 μm, the filler is nowadays usually ground quartz or else a glass ceramic having an average particle size of 8-12 μm. Macro-filled composites have the best wear resistance, but are extremely difficult to polish to a high gloss due to the particle size. During the polishing, the voluminous filler particles break out of the filling, leaving small holes, and the splinters of filler that have broken out exert an emery effect on the remaining moulding material, and so the macro-filled composites cannot be polished to a high gloss and have a fundamental aesthetic deficit.

In order to meet the demand for improved aesthetics, the group of micro-filled dental composite materials was developed. A characteristic feature of this group is the exceptionally small particle size of the composite fillers which consist primarily of amorphous silica and have an average particle size of about 0.04 μm. This small particle size results in an extremely large particle surface area, which in turn, due to intensive interaction forces between the particle surfaces, places an early limit on the filler loading of the composite material. In general, not more than 50% by weight of filler can be added to micro-filled composite materials since the material is then no longer processable due to excessively high viscosity. This composite class can be polished to a high gloss, exhibits excellent refractive properties and meets all criteria for an extremely aesthetic dental material. However, as a result of the low filler content compared to the macro-filled dental composites, micro-filled materials have greatly reduced mechanical properties such as abrasion, tensile strength, excessively high shrinkage, etc.

In attempting to combine the high-gloss polishability of the micro-filled composite materials with the good mechanical properties of macro-filled composites, the class of "hybrid composites" was developed. The filler used here is a mixture of conventional glass having a particle size of 0.6-1.5 μm and of nanoscale particles of 0.01-0.05 μm. In general, the quantitative proportion of the nanoscale silica particles is 7-15% by weight. The total filler content may be up to 80% by weight. Due to the great variation in particle sizes, it is thus possible to achieve an extremely compact packing density of the filler particles, with smaller particles coming to rest in the interstices between the larger particles.

The hybrid composites were the first malleable dental composites to be developed, in the early 1980s. The aim was to introduce a maximum amount of filler into the system in order to achieve the best mechanical values, such as surface hardness, abrasion resistance, wear resistance, compressive strength, tensile strength, polymerization shrinkage, fracture resistance, and also malleability and modellability. The best malleable dental filling composites nowadays, with peak values in their mechanical properties, have a filler content of up to 92% by weight.

In the early 1990s, an attempt was made, as an alternative, to improve dental filling treatment by extremely free-flowing composites. By contrast with the highly filled malleable systems, clinically excellent fillings were to be achieved here by means of a system that readily adapts to the cavity margins and hence leads to extremely marked adaptation between the dental composite and the dentine. The intention here was to prevent the formation of secondary caries, which forms at the marginal gaps between the natural hard substance of the tooth and the filling composite. The best current flow systems have a filler content of about 80% by weight.

In dental filling treatment, there are thus two opposing concepts for arriving at optimal restorations. Firstly, there are malleable and condensable composites which, due to the high filler content, have low polymerization shrinkage, high mechanical values of surface hardness, abrasion resistance, wear resistance and compressive strength, and there secondly exist highly free-flowing composites which, due to their rheological properties, have extremely high marginal adaptation to the cavity walls. Thus, a dentist nowadays can first use a flow material that assures good marginal gap integrity in order then to use a malleable composite to fill the majority of the cavity and thus ensure good mechanical properties of the restoration. A disadvantage of this method is the use of two method steps with different materials.

Toward the end of the 1990s, the first attempts were made to combine the two concepts by prior heating of the composite: the malleable, modellable composite was no longer to be applied to the cavity from its compule at room temperature, but was first to be preheated in a heating unit. The change in temperature was to reduce the viscosity of the dental composite, simplify the ejection of the composite and result in excellent marginal adaptation to the cavity walls (J. Friedman, Thermally assisted polymerization of composite resins, Contemp. Esthet. Restor. Pract., 7, 46, 2003 and H. E. Strassler, R. D. Trushkowsky, Predictable restoration of Class 2 preparations with composite resin, Dent. Today, 23, 93-99, 2004). It was quickly recognized that it was possible to improve the flow characteristics of commercial composites by heating beforehand, but the results were very different according to the composite type. Moreover, what was not achieved was such a markedly reduced viscosity in the preheated composites by comparison with the flow systems that were employed at room temperature (J. S. Blalock, R. G. Holmes, F. A. Rueggeberg, Effect of temperature on uncured composite film thickness, J. Prothet. Dent., 96, 424-432, 2006). Already in the early patent literature, there were the first publications that protected the method of preheating dental composites and corresponding devices for heating, and for ejection of the heated compules. Mention should be made here of the patents to J. Friedmann, for example U.S. Pat. No. 6,236,020 B1 (method), U.S. Pat. No. 6,320,162 B1 (device), U.S. Pat. No. 6,312,254 B1 (dispenser), U.S. Pat. No. 6,616,448 B2 (dispenser), U.S. Pat. No. 7,015,423 B2 (device) and U.S. Pat. No. 7,097,452 B2 (compule). This equipment, which is now commercially available for heating of dental filling composites, can be used chairside by the dentist.

Proceeding from the J. Friedman patents relating to heating of dental composite materials, there have been a multitude of scientific papers on this topic since the early 2000s. This study focused mainly on the influence of the elevated temperature on the physical properties and clinical performance of composites. Frequently, parameters such as flexural strength, modulus of elasticity, surface hardness, volume shrinkage, shrinkage stress and degree of conversion were studied. In addition, marginal adaptation and microleakage and the temperature effects on the pulp were studied.

There were extensive studies with regard to polymerization kinetics with light curing under the conditions of a moderately elevated temperature. For instance, it was found that the double bond conversion with light curing and at a temperature of 54.5° C. was significantly faster and higher in comparison with light curing at room temperature. The extent of the "post-gel phase" was correspondingly shorter. It was concluded, on the basis of these findings, that the properties of the polymer had to be improved (M. Trujillo, S. M. Newmann, J. W. Stansburry, Use of near-IR to monitor the influence of external heating on dental composite photopolymerization, Dent. Mater. 20, 766-777, 2004).

On the other hand, an elevated network density was also to lead to higher polymerization shrinkage and hence exert an adverse effect on the marginal adaptation of the dental composite (U. Lohbauer, S. Zinelis, C. Rahiotis, A. Petschelt, G. Eliades, The effect of resin composite preheating on monomer conversion and polymerization shrinkage, Dent. Mater. 25, 514-519, 2009).

In addition to the studies relating to polymerization shrinkage, there were supplementary studies relating to polymerization stress, which likewise increased with rising double bond conversion (F. C. Calheiros, M. Daronch, F. A. Rueggeberg, R. R. Braga, Effect of temperature on composite polymerization stress and degree of conversion, Dent. Mater. 30, 613-618, 2014).

However, the results of these studies were viewed critically since the above studies were all conducted isothermally, because these conditions do not correspond to the actual clinical situation in which the dentist takes the preheated compule from the heating device, inserts it into a dispenser and then ejects the material into the prepared cavity. The dentist then works and shapes the material, and so a prolonged period passes before the composite is cured. It was estimated that the composite material that has been preheated to 60° C., from the time when it is taken from the heating device, cools down by 50% within the next 2 minutes and has lowered its temperature by 90% after 5 minutes (J. S. Blalock, R. G. Holmes, F. A. Rueggeberg, Effect of temperature on uncured composite film thickness, J. Prothet. Dent., 96, 424-432, 2006).

Once the dental composite has been applied, a thermal equilibrium is reached possibly very rapidly. Under these non-isothermal conditions, which are possibly of greater clinical relevance, the correlation between marginal adaptation, double bond conversion and the mechanical properties of cured dental composites was studied once more. It was found this time that there is no difference in the mechanical properties and the monomer conversion between preheated and non-preheated dental composites, but improved adaptation of the preheated composite to the walls of the cavity was found (N. R. Froes-Salgado, L. M. Silva, Y. Kawano, C. Francci, A. Reis, A. D. Loguercio, Composite pre-heating: Effects on marginal adaptation, degree of conversion and mechanical properties, Dent. Mater. 26, 908-915, 2010).

The results of the scientific studies are thus—taking account of the clinical situation that very substantially corresponds to the conditions in the dental practice on use of the dental preparations—positive and consistent overall.

The temperature-dependent reduction in viscosity, by contrast, has been studied only relatively rarely and, if so, usually only indirectly. These indirect methods are based on the increased flowability of the composite at elevated temperature and hence lower viscosity. For this purpose, a small amount of composite is pressed between two glass plates by a defined force. Subsequently, either the thickness as "film thickness" or the diameter as "flow" or "flowability" is determined. J. Friedman himself found a reduction in film thickness of 32% at a temperature of 60° C. compared to 22.2° C. (EP 1 151 728 B1). J. S. Blalock found, for different composites, a reduction in film thickness in the range from 4% to 77% on heating to 60° C. by comparison with 23° C. (J. S. Blalock et al., Effect of temperature on unpolymerized composite resin film thickness, J. Prosthet. Dent. 2006, 96 (6), 424-423). J. da Costa found, for different composites, a reduction in the film thickness of up to 40% on heating to 68° C. by comparison with 23° C. (J. da Costa et al., Effect of heat on the flow of commercial composites, Am. J. Dent. 2009, 22 (2), 92-96). M. Goulart found, for different composites, a reduction in film thickness of up to 24% on heating to 64° C. by comparison with 21° C. (M. Goulart et al., Effect of pre-heating composites on film thickness, Journal of Research in Dentistry, 2013, 1 (4), 274-280). S. Deb found, for different composites, an increase in flowability of up to 55% on preheating to 60° C. by comparison with 22° C. (S. Deb et al., Pre-warming of dental composites, Dental Materials 2011, 27, e51-e59).

S. Lucey investigated the direct effect of heating on viscosity. A reduction in viscosity of about 55% on heating to 60° C. by comparison with 24° C. was observed (S. Lucey et al., Effect of pre-heating on the viscosity and microhardness of a resin composite, Journal of Oral Rehabilitation 2010, 37, 278-282).

It is immediately apparent that all these studies have been conducted on conventional dental composites that are intended for application at room temperature and have not been specially developed for the operation of heating prior to application. Over the last few years, there have been any number of patent specifications relating to heating devices with which dental composites can be preheated and applied. To our knowledge, there are no studies or studies aimed specifically at the chemical composition of a dental composite that is exposed to heating prior to application.

The problem addressed by the invention was thus that of providing a dental composite that has the good mechanical properties of highly filled, and hence malleable and modellable dental composites, such as high flexural strength (for example about 130 MPa to ISO 4049), high surface hardness (for example micro-Vickers hardness of about 200 MHV), high abrasion resistance (for example ACTA-3 media abrasion, 200 000 cycles about 18 μm), high wear resistance, high compressive strength (for example analogously to ISO 9917 about 440 MPa), high tensile strength and high fracture resistance, and also low polymerization shrinkage (for example about 1.6% by the bonded disc method) and hence also low polymerization stress (for example about 6.7 MPa by the Bioman method); in addition, it should also show the good rheological properties of flow composites.

In short, the method from the prior art, i.e. the supply of a cavity with two different filling composites, a flow material and a malleable material, is to be simplified such that only a single material is now sufficient for cavity supply.

The present invention takes particular account of the following considerations:

For achievement of excellent adaptation of a dental material to cavity margins and hence for achievement of higher adaptation between the dental material and the dentine, the dentist requires a free-flowing dental material which is sufficiently low viscosity at the treatment temperature, i.e., for example, at a temperature in the range from 50° C. to 60° C.

For the preparation of such a treatment, the dentist requires a system composed of dental material and application device, which he can handle easily and reliably at a lower (preparation) temperature.

A further problem addressed by the present invention was therefore that of specifying a dental material and an application device comprising such a dental material, said dental material being reliably and easily handled at a customary preparation temperature (an example of a customary temperature is 20° C.) and simultaneously enabling, at a customary treatment temperature (an example of a customary temperature is 50° C.), good adaptation characteristics and high adaptation between dental material and dentine.

In a first aspect of the present invention, the stated problem is solved by a dental, light-curable, one-component composite composition, as defined in the claims.

In a further aspect of the present invention, the problem is solved by a device for application of a composite composition, as defined in the appended claims.

The dental, light-curable, one-component composite composition according to the invention comprises: (A) monomers, (B) fillers, and (C) initiators; it is characterized in that
the viscosity $\eta_{20}$ of the composite composition at 20° C. is greater than 400 Pa*s and
the viscosity $\eta_{50}$ of the composite composition at 50° C. is less than 150 Pa*s and
the quotient $\eta_{50}/\eta_{20}$ of the viscosity of the composite composition at 50° C. and the viscosity of the composite composition at 20° C. is less than 0.125.

The device according to the invention for application of a composite composition comprises a cavity at least partly filled with an amount of a composite composition according to the invention
and
an application tip connected to the cavity and having an exit opening for the composite composition.

In the state of the art so far, a different approach has been taken to solve corresponding technical problems. For example, VOCO GmbH, Cuxhaven, Germany sells dental materials in an overrun-free, non-dripping syringe equipped with special technology (NDT=non-dripping technology). Corresponding syringes are disclosed in document EP 2 016 962 B. NDT syringes and comparable syringes from other manufacturers solve the technical problems associated with the use of low-viscosity materials by a technical engineering route via configuration of the application device. The present invention chooses a diametrically different approach to a solution and concentrates on a rheologically advantageous configuration of the composite compositions to be used. The present text sets out in detail how the person skilled in the art, using customary constituents, arrives at a dental composite composition that achieves the different requirements according to the invention with regard to viscosity at firstly 20° C. and secondly 50° C. By virtue of their properties, the composite compositions according to the invention contribute to reducing or preventing the risk of workplace contamination at a preparation temperature of 20° C. (see the discussion in EP 2 016 962 B). More particularly, the composite compositions according to the invention contribute to the fact that, at a processing temperature of 20° C., a premature release of the composite composition with use of customary application devices is made more difficult in comparison with standard commercial composite compositions which are particularly low in viscosity already at 20° C.

Only by the preheating of a composite composition according to the invention from the preparation temperature (especially 20° C.) to the treatment temperature (especially 50° C.) the viscosity is reduced to such an extent that the release of the composite composition from an application device is particularly easy and, at the same time, the medical and chemical specifications are achieved (adaptation characteristics). At the treatment temperature (especially 50° C.), the application device will regularly be used by a dentist who has particular training to use such application devices (with their contents that are then of low viscosity) properly and safely. At the preparation temperature (especially 20° C.), the application device according to the invention (with the composite composition present therein) can also be utilized by less trained personnel (for example a dentist's assistant), since the risk of premature material release is reduced.

A dental, light-curable, one-component composite composition according to the invention preferably has a viscosity $\eta_{20}$ at 20° C. of greater than 800 Pa*s, more preferably of greater than 1200 Pa*s and/or a viscosity $\eta_{50}$ at 50° C. of less than 120 Pa*s, more preferably of less than 90 Pa*s and/or a quotient $\eta_{50}/\eta_{20}$ of the viscosity of the composite composition at 50° C. and the viscosity of the composite composition at 20° C. of less than 0.1.

A dental, light-curable, one-component composite composition according to the invention preferably has a viscosity $\eta_{37}$ at 37° C. of greater than 400 Pa*s. Composite compositions of this kind have good modellability at intraoral temperature.

The remarks relating to the viscosities of the dental, light-curable, one-component composite compositions according to the invention are analogously applicable to the uses according to the invention of the composite compositions and the methods according to the invention. In particular, preferred viscosities (or their quotients) of dental, light-curable, one-component composite compositions according to the invention are also preferred viscosities (or their quotients) in the case of the use according to the invention of these composite compositions and in the methods according to the invention, and vice versa.

With regard to fixing of the viscosity limits see FIG. 1 and further down.

More particularly, the problem is solved by a dental, light-curable, one-component composite composition, preferably for production of a dental filling material, lining material, luting material or fissure sealant, comprising:
(A) monomers in an amount of 6% to 35% by weight, based on the composite composition, preferably 10% to 35% by weight, more preferably 10% to 25% by weight,
(B) fillers in an amount of 65% to 93% by weight, based on the composite composition, preferably 65% to 89% by weight, more preferably 75% to 89% by weight,
(C) initiators in an amount of 0.001% to 3% by weight, based on the amount of the composite composition,
(D) further additives in an amount of 0.001% to 5% by weight, based on the amount of the composite composition.

The remarks relating to the monomers (A) usable in accordance with the invention apply both to the use of the monomers in the dental, light-curable, one-component composite compositions according to the invention and to use in the methods according to the invention. More particularly, monomers usable with preference in dental, light-curable, one-component composite compositions according to the invention are also usable with preference in the methods according to the invention, and vice versa.

In a particular embodiment, constituent (A) of the dental, light-curable, one-component composite composition comprises the mixture of at least
(A-i) one first monomer substance and
(A-ii) one second monomer substance,
wherein
the viscosity $\eta_{20}$ of the second monomer substance (A-ii) at 20° C. is greater than 100 Pa*s,
the viscosity $\eta_{20}$ of the first monomer substance (A-i) at 20° C. is greater than 100 mPa*s,
the viscosity of the second monomer substance (A-ii) at 20° C. is greater than that of the first monomer substance (A-i) and
the mass ratio of the first monomer substance (A-i) to the second monomer substance (A-ii) is in the range from 2:1 to 1:10,
wherein the second monomer substance (A-ii) preferably contains at least 40% by weight of 2,2-bis[4-(2-hydroxy-3-methacryloyloxypropoxy)phenyl]propane (bis-GMA) and/or light-curable derivatives of diisocyanatodiphenylmethane (MDI) and/or light-curable derivatives of tetramethyl-m-xylylene diisocyanate (TMXDI), wherein the percentage by weight is based on the total mass of the monomers (A).

The studies that the inventors have conducted in the context of the present invention show that, when constituents (A) to (D) are used in the amounts specified (preferably in the ranges of amount that are specified as preferred), the viscosity requirements characteristic of the invention can be established particularly efficiently. The person skilled in the art will be guided by Examples 1-34 further down in the design of composite compositions according to the invention, and—if desired—perform variations and in so doing take note of the requirements relating to the viscosity at 20° C. and 50° C.

In the embodiments and examples which follow,
(A1) corresponds to the light-curable bi- or tricyclic compounds $Q(Y_xZ_e)_b$,
(A2) corresponds to bis-GMA (2,2-bis[4-(2-hydroxy-3-methacryloyloxypropoxy)phenyl]-propane) and/or the light-curable derivatives of MDI (diisocyanatodiphenylmethane) and/or the light-curable derivatives of TMXDI,
(A3) corresponds to the light-curable monomers, which are substances having one, two or more ethylenic groups, for example, but not limited to, the (meth)acrylate monomers that are typically used in dental chemistry and cannot be assigned to (A1) and (A2),
(A4) corresponds to the light-curable bi- or tricyclic compounds $Q(Y_xZ_e)_b$, to 7,7,9-trimethyl-3,14-dioxa-4,13-dioxo-5,12-diazahexadecane 1,16-dioxydi(meth)acrylate (UDMA), to 7,9,9-trimethyl-3,14-dioxa-4,13-dioxo-5,12-diazahexadecane 1,16-dioxydi(meth)acrylate, to 7,9-dimethyl-3,14-dioxa-4,13-dioxo-5,12-diazahexadecane 1,16-dioxydi(meth)acrylate, to 3,14-dioxa-4,13-dioxo-5,12-diazahexadecane 1,16-dioxydi(meth)acrylate, to 1,5,5-trimethyl-1-[(2-methacryloyloxyethyl)carbamoylmethyl]-3-(2-methacryloyloxyethyl)carbamoylcyclohexane, to 7,7,9,9-tetramethyl-3,14-dioxa-4,13-dioxo-5,12-diazahexadecane 1,16-dioxydi(meth)acrylate, to 2,7,7,9,15-pentamethyl-3,14-dioxa-4,13-dioxo-5,12-diazahexadecane 1,16-dioxydi(meth)acrylate, to 2,7,9,9,15-pentamethyl-3,14-dioxa-4,13-dioxo-5,12-diazahexadecane 1,16-dioxydi(meth)acrylate, to 2,7,9,15-tetramethyl-3,14-dioxa-4,13-dioxo-5,12-diazahexadecane 1,16-dioxydi(meth)acrylate, to 2,15-dimethyl-3,14-dioxa-4,13-dioxo-5,12-diazahexadecane 1,16-dioxydi(meth)acrylate, to 1,5,5-trimethyl-1-[(1-methacryloyloxypropan-2-yl)carbamoylmethyl]-3-(1-methacryloyloxypropan-2-yl)carbamoylcyclohexane, to 2,7,7,9,9,15-hexamethyl-3,14-dioxa-4,13-dioxo-5,12-diazahexadecane 1,16-dioxydi(meth)acrylate, to bisEMA (alkoxylated bisphenol A di(meth)acrylate with n=2-6), to the poly(meth)acrylates containing hydroxyl groups, to the alkoxylated poly(meth)acrylates containing hydroxyl groups, and to the light-curable chain-like and/or cyclic and/or cage-type polysiloxanes,
(A5) corresponds to the light-curable monomers (A3) excluding (A4).

In a preferred configuration, the monomers (A) consist of
(A1) 10% to 60% by weight, preferably 20% to 50% by weight, more preferably 25% to 40% by weight, of light-curable bi- or tricyclic compounds $Q(Y_xZ_e)_b$ wherein
Q denotes a saturated or olefinically unsaturated bi- or tricyclic structural element,
each index b is a natural number selected from the group of the natural numbers 1, 2, and 3,
each Z denotes a light-curable group,
each index e is a natural number selected from the group of the natural numbers 1, 2 and 3,
each Y in the structure $Q(Y_xZ_e)_b$ with x=1 denotes a structural element which connects the structural element Q to e structural elements Z and which denotes a straight or branched alkylene group, wherein the alkylene group may be interrupted by oxygen atoms, and each index x is 0 or 1,
(A2) 40% to 90% by weight, preferably 50% to 80% by weight, more preferably 60% to 75% by weight, of 2,2-bis[4-(2-hydroxy-3-methacryloyloxypropoxy)phenyl]propane (bis-GMA) and/or light-curable derivatives of diisocyanatodiphenylmethane (MDI) and/or light-curable derivatives of tetramethyl-m-xylylene diisocyanate (TMXDI),
(A3) 0% to 15% by weight, preferably 0% to 10% by weight, more preferably 0% to 5% by weight, of further free-radically polymerizable monomers that cannot be assigned to (A1) or (A2),
wherein the percentages by weight (A1), (A2) and (A3) are based on the total mass of the monomers (A).

The present invention also relates to a dental, light-curable, one-component composite composition comprising:
(A) monomers
(B) fillers and
(C) initiators, wherein
the monomers (A) consist of
(A1) 10% to 60% by weight, preferably 20% to 50% by weight, more preferably 25% to 40% by weight, of light-curable bi- or tricyclic compounds $Q(Y_xZ_e)_b$ wherein
Q denotes a saturated or olefinically unsaturated bi- or tricyclic structural element,
each index b is a natural number selected from the group of the natural numbers 1, 2, and 3,
each Z denotes a light-curable group,
each index e is a natural number selected from the group of the natural numbers 1, 2 and 3,
each Y in the structure $Q(Y_xZ_e)_b$ with x=1 denotes a structural element which connects the structural element Q to e structural elements Z and which denotes a straight or branched alkylene group, wherein the alkylene group may be interrupted by oxygen atoms, and each index x is 0 or 1, (A2) 40% to 90% by weight, preferably 50% to 80% by weight, more preferably 60% to 75% by weight, of 2,2-bis[4-(2-hydroxy-3-methacryloyloxypropoxy)phenyl]propane (bis-GMA) and/or light-curable derivatives of diisocyanatodiphenylmethane (MDI) and/or light-curable derivatives of tetramethyl-m-xylylene diisocyanate (TMXDI), (A3) 0% to 15% by weight, preferably 0% to 10% by weight, more preferably 0% to 5% by weight, most preferably 0% by weight, of further free-radically polymerizable monomers that cannot be assigned to (A1) or (A2), wherein the percentages by weight of (A1), (A2) and (A3) are based on the total mass of the monomers (A).

(A1) comprises the following aliphatic bi- or tricyclic systems, the unsubstituted structures of which are by way of example as follows:

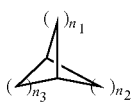

wherein $n_1$, $n_2$ and $n_3$ each independently denote a natural number from 1 to 8, preferably a natural number from 1 to 4.

The following examples are mentioned here:
when $n_1=n_2=1$; $n_3=2$ bicyclo[2.1.1]hexane
when $n_1=1$; $n_2=n_3=2$ bicyclo[2.2.1]heptane
when $n_1=n_2=1$; $n_3=3$ bicyclo[3.1.1]heptane
when $n_1=n_2=n_3=2$ bicyclo[2.2.2]octane
when $n_1=n_2=1$; $n_3=4$ bicyclo[4.1.1]octane
when $n_1=1$; $n_2=2$; $n_3=3$ bicyclo[3.2.1]octane
when $n_1=1$; $n_2=2$; $n_3=4$ bicyclo[4.2.1]nonane
when $n_1=n_2=2$; $n_3=4$ bicyclo[4.2.2]decane Some disubstituted bicyclic systems are shown by way of example below:

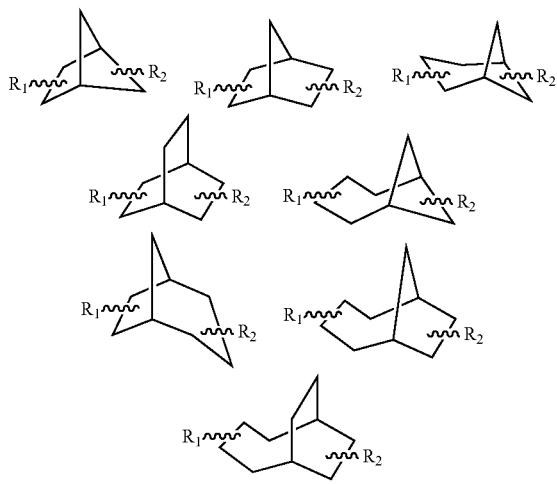

wherein R1 and R2 in each case denote the other radicals in the compound.

Examples of bicyclic structural elements are the bicyclo[1.1.1]pentane, bicyclo[2.1.1]hexane, bicyclo[2.2.1]heptane, bicyclo[3.1.1]heptane, bicyclo[2.2.2]octane, bicyclo[4.1.1]octane, bicyclo[3.2.1]octane, bicyclo[4.2.1]nonane, bicyclo[3.3.1]nonane, bicyclo[5.1.1]nonane, bicyclo[3.2.2]nonane, bicyclo[6.1.1]decane, bicyclo[5.2.1]decane, bicyclo[4.2.2]decane, bicyclo[3.3.2]decane, bicyclo[7.1.1]undecane, bicyclo[6.2.1]undecane, bicyclo[5.2.2]undecane, bicyclo[4.3.2]undecane, bicyclo[3.3.3]undecane, bicyclo[8.1.1]dodecane, bicyclo[7.2.1]dodecane, bicyclo[6.2.2]dodecane, bicyclo[5.3.2]dodecane, bicyclo[4.3.3]dodecane, bicyclo[4.4.2]dodecane, bicyclo[5.4.1]dodecane structural element, and even higher structural elements such as the corresponding tridecanes, tetradecanes, pentadecanes, etc.

For unsubstituted tricyclic systems, for example, the following structures are possible:

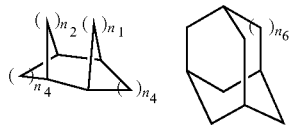

wherein $n_1$, $n_2$, $n_3$, $n_4$ and $n_6$ may each independently denote a natural number from 0 to 5.

Examples include:
when $n_1=2$; $n_2=0$; $n_3=2$; $n_4=3$ tricyclo[4.3.2.0$^{2,5}$]undecane
when $n_1=0$; $n_2=1$; $n_3=2$; $n_4=3$ tricyclo[5.2.1.0$^{2,6}$]decane
when $n_1=0$; $n_2=2$; $n_3=2$; $n_4=3$ tricyclo[5.2.2.0$^{2,6}$]undecane
when $n_1=2$; $n_2=0$; $n_3=2$; $n_4=2$ tricyclo[4.2.2.0$^{2,5}$]decane
when $n_6=1$ tricyclo[3.3.1.1$^{3,7}$]decane Some examples of di- or trisubstituted tricyclic systems are shown below:

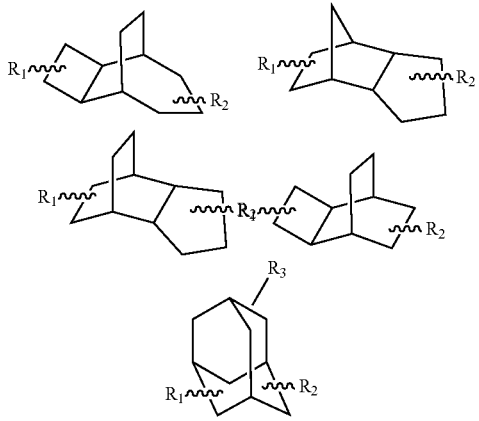

wherein R1, R2 and R3 in each case denote the other radicals in the compound.

Examples of tricyclic structural elements are the tricyclo[3.2.1.0$^{2,6}$]octane, tricyclo[4.2.1.0$^{2,6}$]nonane, tricyclo[5.2.1.0$^{2,6}$]decane, tricyclo[6.2.1.0$^{2,6}$]undecane, tricyclo[7.2.1.0$^{2,6}$]dodecane structural elements, or the tricyclo[4.2.1.1$^{2,5}$]decane, tricyclo[4.3.1.1$^{2,5}$]decane, tricyclo[4.4.1.1$^{2,5}$]decane, tricyclo[2.2.1.0$^{2,6}$]heptane, tricyclo[2.2.2.0$^{2,6}$]octane, tricyclo[3.2.2.0$^{2,6}$]nonane, tricyclo[3.3.1.1$^{3,7}$]decane, tricyclo[3.2.1.1$^{3,7}$]nonane, tricyclo[4.2.2.2$^{2,5}$]dodecane, tricyclo[4.3.2.2$^{2,5}$]tridecane, tricyclo

[4.4.2.2$^{2,5}$]tetradecane, tricyclo[4.2.1.0$^{3,7}$]nonane, tricyclo [4.4.1.1$^{1,5}$]dodecane, tricyclo[6.2.1.0$^{2,7}$]undecane, tricyclo [5.2.2.0$^{2,6}$]undecane, tricyclo[6.2.2.0$^{2,7}$]dodecane, tricyclo [4.3.2.0$^{2,5}$]undecane, tricyclo[4.2.2.0$^{2,5}$]decane or tricyclo [5.5.1.0$^{3,11}$]tridecane structural elements.

In a preferred embodiment, the structure of the polyalicyclic structural element derives from a bicyclic [a.c.d] hydrocarbon. The letters a, c and d are natural numbers and have the meaning of the IUPAC nomenclature. The sum total of a, c and d is preferably in the range from 3 to 13, more preferably in the range from 4 to 7.

In a further preferred embodiment, the structure of the polyalicyclic structural element derives from a tricyclic [a.c.d.f]-hydrocarbon. The sum total of a, c, d and f is preferably in the range from 6 to 12, more preferably in the range from 7 to 9.

In a preferred embodiment, the structure of the polyalicyclic structural element derives from a tricyclic [a.2.1.0$^{2,(a+1)}$] hydrocarbon wherein a in each case may denote the number 3, 4, 5, 6 or 7.

In a further preferred embodiment, the structure of the polyalicyclic structural element derives from a tricyclic [a.2.2.0$^{2,(a+1)}$] hydrocarbon wherein a in each case may denote the number 3, 4, 5, 6 or 7.

In a further preferred embodiment, the structure of the polyalicyclic structural element derives from a tricyclic [a.3.1.1] hydrocarbon wherein a in each case may denote the number 3, 4, 5, 6 or 7.

The light-curable group Z denotes a structural element selected from the group consisting of —O—(C=O)—CH=CH$_2$, —O—(C=O)—C(CH$_3$)=CH$_2$, —(C=O)—CH=CH$_2$, —(C=O)—C(CH$_3$)=CH$_2$, —CH=CH$_2$, —C(CH$_3$)=CH$_2$ and —O—CH=CH$_2$, preference being given to the (meth)acrylates.

The connecting element Y denotes a straight or branched alkylene group, wherein the alkylene group may be interrupted by oxygen atoms and in that case forms ethers and/or polyalkylene glycols.

In order to arrive at the light-curable bi- or tricyclic monomers (A1), the starting materials are preferably the correspondingly alcohol-substituted polyalicyclic hydrocarbons named above, or their alkoxylated variants that are esterified by simple reaction with (meth)acrylic acid to give the monomers (A1).

For esterification of the commercially available compounds, preference is given to using bicyclo[2.2.1]heptane-2,7-diol, bis(hydroxymethyl)bicyclo[2.2.1]heptane, [5-(hydroxymethyl)-6-bicyclo[2.2.1]hept-2-enyl]methanol, tricyclo[3.3.1.1$^{3,7}$]decane-1,3-diethanol, [6-(hydroxymethyl)-6-bicyclo[2.2.1]hept-2-enyl]methanol, tricyclo[3.3.1.1$^{3,7}$]decane-1,3-diol, bis(hydroxymethyl)tricyclo[5.2.1.0$^{2,6}$]decane, and the respective corresponding alkoxylated variants, the most preferred being bis(hydroxymethyl)tricyclo[5.2.1.0$^{2,6}$]decane and its alkoxylated variants and bis(hydroxymethyl)bicyclo[2.2.1]heptane and its alkoxylated variants.

Using the example of the most-preferred variants, the syntheses of the starting substances are elucidated in detail by way of example:

Bis(hydroxymethyl)tricyclo[5.2.1.0$^{2,6}$]decane can be purchased commercially and can be sourced, for example, as the dicidol mixture of the isomeric compounds 3,8-bis (hydroxymethyl)tricyclo[5.2.1.0$^{2,6}$]decane and 4,8-bis(hydroxymethyl)tricyclo[5.2.1.0$^{2,6}$]decane, and 3,9-bis(hydroxymethyl)tricyclo[5.2.1.0$^{2,6}$]decane and 4,9-bis (hydroxymethyl)tricyclo[5.2.1.0$^{2,6}$]decane.

However, the bis(hydroxymethyl)tricyclo[5.2.1.0$^{2,6}$]decanes can alternatively be synthesized in a simple manner proceeding from dicyclopentadiene (tricyclo[5.2.1.0$^{2,6}$] deca-3,8-diene). Dicyclopentadiene is easily accessible by dimerization in a Diels-Alder reaction. Hydroformylation of dicyclopentadiene then gives bis(hydroxymethyl)tricyclo [5.2.1.0$^{2,6}$]decane. According to the synthesis route, it is possible to obtain bis(hydroxymethyl)tricyclo[5.2.1.0$^{2,6}$]decanes substituted at different positions. Thus in published documents JP 7-206740, EP 1 112 995 B1 or EP 0 049 631 B1 specifications are provided on how, for example the 8,9-bis(hydroxymethyl)tricyclo[5.2.1.0$^{2,6}$]decane can be prepared. DE 103 52 260 B3, by contrast, describes methods for preparing 3(4),8(9)-bis(hydroxymethyl)tricyclo[5.2.1.0$^{2,6}$]decane. The notation of the positions of the hydroxymethyl groups 3(4) and 8(9) denotes 3 or 4, 8 or 9.

3(4),8(9)-Bis(hydroxymethyl)tricyclo[5.2.1.0$^{2,6}$]decane, which is commercially available and usable as starting compound for preparation of the most preferred monomers (A1), thus contains hydroxymethyl groups both at position 3 or 4 and in position 8 or 9. It is then possible by adding on alkoxides, generally in amounts of 1 to 10 mol, especially ethylene oxide, propylene oxide, butylene oxide, etc., in the presence of basic catalysts, by known methods, to synthesize the corresponding polyether polyols. EP 0 023 686 B1 contains exact preparation methods for this purpose.

2,5(2,6)-Bis(hydroxymethyl)bicyclo[2.2.1]heptane is commercially available or can be obtained from norbornadiene (preparable from cyclopentadiene and ethyne) by hydroformylation and subsequent reduction of the diformylnorbornane to give norbornanediol. The hydroformylation can be effected either in a conventional or non-conventional manner.

In the conventional method, norbornadiene is reacted with the synthesis gas CO/H$_2$ (1:1) in an organic solvent, for example toluene, in an autoclave under pressure (100 atm) and high temperatures (100° C.) in the presence of a catalyst. After a reaction time of 90 minutes, no substrate is detectable any longer and the reaction is complete with formation of the dialdehydes with high selectivity. The main components formed are the two isomers of the exo,exo-dialdehyde. Catalysts used are [Pt(C$_2$H$_4$)(dppb)]/CH$_3$SO$_3$H. The abbreviation "dppb" denotes 1,4-bis(diphenylphosphino)butane. An exact preparation method is specified in Journal of Organometallic Chemistry, 447, 153-157, 1993 in a paper entitled "Hydroformylation of norbornene and 2,5-norbornadiene catalysed by platinum-(0)-alkene complexes in the presence of methanesulfonic acid: determination of the stereochemistry of the reaction". Catalyst metals used may also be cobalt and rhodium in the form of their hydridocarbonyl species (HM(CO)$_4$), for example based on hydridocobalt tetracarbonyl (HCo(CO)$_4$).

In the non-conventional method, i.e. in supercritical carbon dioxide, hydrogen and carbon monoxide react in the catalytic conversion of the olefins to the aldehydes under far less severe conditions compared to the conventional method. At just 20 bar and 100° C. in the presence of Rh/4-H$^2$F$^6$-TPP, the reaction proceeds almost quantitatively within 30 minutes with a proportion of 95% of dialdehydes. In the rhodium-catalysed hydroformylation in supercritical carbon dioxide, the solubility of the Rh catalyst in CO$_2$ is increased by derivatizing the triphenylphosphine ligand with perfluoroalkyl groups, with reduction of the electronic influence to the metal centre by means of two CH$_2$ groups, called spacers. The acronym 4-H$^2$F$^6$-TPP thus means that, in position 4, i.e. in the para position of the aromatic ring (viewed from the phosphorus atom), there are at first 2 connecting CH$_2$ groups, followed by 6 CF$_2$ groups. Exact preparation methods can be found in the thesis by H. Stemmer, 2001, Friedrich-Schiller University of Jena, entitled "Homogene Katalyse in überkritischem Kohlendioxid: Analogien und Unterschiede zu konventionellen Lösungsmitteln" [Homogeneous Catalysis in Supercritical Carbon Dioxide: Analogies and Differences from Conventional Solvents].

(A2) comprises

1.) bis-GMA (2,2-bis[4-(2-hydroxy-3-methacryloyloxypropoxy)phenyl]propane), which can be obtained either by reaction of bisphenol A with glycidyl (meth)acrylate or by reaction of the diglycidyl ether of bisphenol A with (meth)acrylic acid.

Advantageously, the product is prepared by the latter synthesis route. For this purpose, the ether is first obtained by reaction of epichlorohydrin (ECH, 1-chloro-2,3-epoxypropane, prepared from allyl chloride (synthesized from propene with chlorine) with hypochlorous acid and subsequent reaction with NaOH) and bisphenol A (BPA; 4,4'-isopropylidenephenol, synthesized from acetone and phenol). Further reaction with methacrylic acid gives bis-GMA. In order to arrive at a bis-GMA that can advantageously be used for preparation of dental composite compositions according to the invention, some details of the synthesis should be noted. The stoichiometric reaction of BPA with ECH (1:2) would theoretically be expected to form a product having 2 terminal epoxy groups and no hydroxyl group with a molecular weight of 350 g/mol. In a first reaction step, the epoxy group of the ECH reacts with the phenoxide ion of the BPA that has formed under the influence of the basic catalyst (NaOH) to generate the chlorohydrin ether. In a second step, the ether is dehydrochlorinated under the influence of the base and the monoglycidyl ether (MGEBA) is formed. The as yet incompletely reacted secondary phenolic hydroxyl group could then react with a second ECH molecule, the above steps could be repeated and the diglycidyl ether of bisphenol A (DGEBA) could form. However, there are now two competing reaction paths available to the MGEBA formed: firstly the already mentioned reaction with ECH to give DGEBA, and secondly the reaction of the MGEBA with further BPA to give diphenols of higher molecular weight, which can in turn react further with ECH. For preparation of a bis-GMA that advantageously finds use in a dental composite composition according to the invention, the reaction between BPA and ECH is conducted with a molar excess of ECH. Particular preference is given to working with a large molar excess, at best in such a way that the ECH assumes the role of the solvent. It should thus be ensured that all phenolic hydroxyl groups are consumed and hence the formation of higher species is suppressed as far as possible.

DGEBA having a minimum level of oligomeric constituents is heated at temperatures between 100 and 150° C. and atmospheric pressure, before the methacrylic acid is added in a molar excess. As soon as the conversion to the ester is greater than 96%, the reaction is stopped after a reaction time of about 24 hours.

U.S. Pat. No. 3,066,112 reports the synthesis of bis-GMA by reaction of bisphenol A with glycidyl (meth)acrylate.

2.) light-curable derivatives of MDI (diisocyanatodiphenylmethane), as described, for example, in the examples of US 2006/0205902 A1.

The MDI is synthesized in a first step by reaction of aniline with formaldehyde in the presence of HCl to give diaminodiphenylmethane and then further in a conventional phosgenation reaction to give the diisocyanate with elimination of HCl. Pure MDI is a solid. For this reason, the starting material used for the synthesis of the light-curable derivatives of MDI for the dental composite compositions according to the invention is the undistilled crude product, the amine used for preparation of the MDI being the unpurified aniline-formaldehyde condensate. What is formed is the correspondingly isomeric liquid substance mixture of the 4,4'-, 2,2'- and 2,4'-MDI compounds. As a result of the condensation character of the formaldehyde-aniline reaction, the reaction product may additionally contain oligomers and therefore be of higher functionality and constitute a complex reaction mixture.

MDI is also commercially available in different purities and compositions, for example from "Covestro" under the "Mondur" trade name, from "BASF" under the "Lupranate" trade name or from "DOW" under the "Isonate" trade name. The variants that are liquid at room temperature are often supplied either as mixtures of the monomeric 4,4'-MDI and 2,4'-MDI isomers or in mixtures having a reduced content of 2,2'-MDI isomer.

Advantageously, light-curable derivatives of MDI are also prepared using what are called "modified MDI compounds". The preparation of these variants is known to the person skilled in the art; they are also commercially available. These include, for example, carbodiimide-modified MDI, allophanate-modified MDI, biuret-modified MDI and polymeric MDI, or combinations of these MDI variants (see also patent specifications U.S. Pat. Nos. 5,319,054 and 5,440,003).

In the isocyanate reactions that are known to the dental chemist—proceeding from liquid MDI—it is possible to synthesize light-curable MDI derivatives for the dental composite compositions according to the invention (see additionally also WO 2018/071920 A1). The term "light-curable derivatives of MDI" is especially understood to mean the preferred compounds that result from the reaction of liquid MDI with alcohols, where the alcohols bear light-curable groups such as unsaturated hydrocarbyl groups, for example —CH=CH$_2$, —C(CH$_3$)=CH$_2$, —CH$_2$—CH=CH$_2$, —CH$_2$—C(CH$_3$)=CH$_2$ and —O—CH=CH$_2$, and preferably bear unsaturated, activated hydrocarbyl groups, for example —O—(C=O)—CH=CH$_2$ and —O—(C=O)—C(CH$_3$)=CH$_2$ or —(C=O)—CH=CH$_2$, —(C=O)—C(CH$_3$)=CH$_2$. The resulting compounds are diurethanes.

MDI can be reacted, for example, with primary alcohols such as 2-hydroxyethyl (meth)acrylate (HEMA), 3-hydroxypropyl (meth)acrylate (3-HPMA), 4-hydroxybutyl (meth)acrylate (4-HBMA) or with secondary alcohols such as hydroxypropyl (meth)acrylate (HPMA), hydroxybutyl (meth)acrylate (HBMA), glycerol di(meth)acrylate (GlyDMA), 2-hydroxy-3-phenoxypropyl (meth)acrylate (HPPMA) to give light-curable MDI derivatives. The isocyanate-alcohol reaction generally proceeds in an uncomplicated, rapid and quantitative manner. The reaction can be conducted at RT (room temperature) or at a temperature set slightly above room temperature in the presence of a very small amount of catalyst. Catalysts used may be tertiary amines, alkaline substances and organometallic compounds. The light-curable derivatives of MDI are preferably prepared using organotin compounds, for example dibutyltin dilaurate, or else compounds of divalent tin, such as tin(II) dioctoate. Alternatively, these reactions can also be conducted with an amine, for example with 1,4-diazabicyclo[2.2.2]octane (DABCO).

For preparation of the MDI-HEMA product, commercially available liquid MDI having a molecular weight of 250 g/mol is reacted with commercially available HEMA. For this purpose, the reactants preheated to 60° C. were weighed in a molar ratio of 1:2 into a previously baked-out reaction vessel and reacted while stirring in the silicone bath that had already been preheated to 60° C. After the blending of the reactants, a few drops of dibutyltin dilaurate were added to the mixture. The HEMA had been stabilized beforehand with BHT. The progress of the reaction was determined by means of IR spectroscopy. The NCO group characteristic of the MDI absorbs within the wave number range from 2250 to 2275 $cm^{-1}$. The band has a high intensity and is not affected by conjugation. After 6 hours, it was no longer possible to detect any isocyanate band. The MDI-HEMA adduct was obtained in a yield of 86% as a pale yellowish oil.

3.) light-curable derivatives of TMXDI, as described in N. Moszner et al. "Synthesis and polymerisation of new multifunctional urethane methacrylates", Die Angewandte Makromolekulare Chemie 265 (1999), 31-35, in N. Moszner et al. "A partially aromatic urethane dimethacrylate as a new substitute for bis-GMA in restorative composites", Dental Materials, 24 2008, 694-699 and in DE 198 03 979 A1.

The term "light-curable derivatives of TMXDI" is understood to mean compounds that result from the reaction of TMXDI with alcohols, where the alcohols bear light-curable groups such as unsaturated hydrocarbyl groups, for example —CH=$CH_2$, —C($CH_3$)=$CH_2$, —$CH_2$—CH=$CH_2$, —$CH_2$—C($CH_3$)=$CH_2$ and —O—CH=$CH_2$, and preferably bear unsaturated, activated hydrocarbyl groups, for example —O—(C=O)—CH=$CH_2$ and —O—(C=O)—C($CH_3$)=$CH_2$ or —(C=O)—CH=$CH_2$, —(C=O)—C($CH_3$)=$CH_2$. The resulting compounds are diurethanes.

The conversions of the isocyanates to light-curable derivatives of TMXDI are effected in an entirely analogous manner to the reactions of MDI to give its light-curable derivatives. The publication by N. Moszner in Angewandte Makromolekulare Chemie and the patent specification explicitly describe the reaction of HEMA and TMXDI to give the TMXDI-HEMA addition product. These texts also contain synthesis methods for further conversions. TMXDI is obtained by reaction of isocyanic acid with m-diisopropenylbenzene (see U.S. Pat. No. 3,290,350). The compound is also commercially available.

(A3) are light-curable monomers that are substances having one, two or more ethylenic groups, for example, but not limited to, (meth)acrylate monomers customarily used in dental chemistry.

The patent literature cites a multitude of compounds that are all diesters of acrylic acid or methacrylic acid and are suitable for use in a light-curable mixture according to the invention.

A light-curable mixture of a dental composite composition according to the invention contains, by way of example, one or more di(meth)acrylate monomers selected from group (A3) consisting of ethylene glycol di(meth)acrylate, alkoxylated ethylene glycol di(meth)acrylate, diethylene glycol di(meth)acrylate, hexane-1,6-diol di(meth)acrylate, triethylene glycol di(meth)acrylate, dodecane-1,12-diol di(meth)acrylate, decane-1,10-diol di(meth)acrylate, bisphenol A di(meth)acrylate, alkoxylated bisphenol A di(meth)acrylate, polyethylene glycol di(meth)acrylate, propylene glycol di(meth)acrylate, dipropylene glycol di(meth)acrylate, tripropylene glycol di(meth)acrylate, tetrapropylene glycol di(meth)acrylate, polypropylene glycol di(meth)acrylate, 7,7,9-trimethyl-3,14-dioxa-4,13-dioxo-5,12-diazahexadecane 1,16-dioxydi(meth)acrylate, butanediol di(meth)acrylate, propanediol di(meth)acrylate, tetraethylene glycol di(meth)acrylate, neopentyl glycol di(meth)acrylate, alkoxylated neopentyl glycol di(meth)acrylate, 2-hydroxypropyl 1,3-di(meth)acrylate, 3-hydroxypropyl 1,2-di(meth)acrylate, pentaerythritol di(meth)acrylate, alkoxylated pentaerythritol di(meth)acrylate, pentaerythritol tri(meth)acrylate, alkoxylated pentaerythritol tri(meth)acrylate, pentaerythritol tetra(meth)acrylate, alkoxylated pentaerythritol tetra(meth)acrylate, dipentaerythritol di(meth)acrylate, alkoxylated dipentaerythritol di(meth)acrylate, dipentaerythritol tri(meth)acrylate, alkoxylated dipentaerythritol tri(meth)acrylate, dipentaerythritol tetra(meth)acrylate, alkoxylated dipentaerythritol tetra(meth)acrylate, dipentaerythritol penta(meth)acrylate, alkoxylated dipentaerythritol penta(meth)acrylate, dipentaerythritol hexa(meth)acrylate, alkoxylated dipentaerythritol hexa(meth)acrylate, trimethylolpropane tri(meth)acrylate, alkoxylated trimethylolpropane tri(meth)acrylate and cyclohexanedimethanol di(meth)acrylate.

In a preferred light-curable mixture according to the invention, component (A3) is present in a proportion of less than 10% by weight, preferably of less than 5% by weight, based on the total mass of the monomers (A).

In a particularly preferred light-curable mixture according to the invention, the optional constituent (A3) is absent.

(A4) are particular light-curable monomers that are likewise possible partners for (A2) in thermally responsive dental compositions, which are well known to the dental chemist and are commonly used in dental compositions.

UDMA is obtained by simple reaction of 2 mol of hydroxyethyl (meth)acrylate (HEMA) with 2,4,4-trimethylhexamethylene diisocyanate (TMDI) and/or 2,2,4-trimethylhexamethylene diisocyanate and is, like bis-EMA or like the (alkoxylated) poly(meth)acrylates containing hydroxyl groups, commercially available.

Further UDMA variants can be produced by reaction of 2 mol of HEMA with 2,4-dimethylhexamethylene diisocyanate (7,9-dimethyl-3,14-dioxa-4,13-dioxo-5,12-diazahexadecane 1,16-dioxydi(meth)acrylate CAS-No.: 865234-08-8), of 2 mol of HEMA with hexamethylene diisocyanate (3,14-dioxa-4,13-dioxo-5,12-diazahexadecane 1,16-dioxydi(meth)acrylate CAS-No.: 34100-36-2), of 2 mol of HEMA with isophorone diisocyanate (1,5,5-trimethyl-1-[(2-methacryloyloxyethyl)carbamoylmethyl]-3-(2-methacryloyloxyethyl)carbamoylcyclohexane CAS-No.: 42405-01-6), of 2 mol of HEMA with 2,2,4,4-tetramethylhexamethylene diisocyanate (7,7,9,9-tetramethyl-3,14-dioxa-4,13-dioxo-5,12-diazahexadecane 1,16-dioxydi(meth)acrylate CAS-No.: 865234-10-2), of 2 mol of hydroxypropyl(meth)acrylate (HPMA) with 2,2,4-trimethylhexamethylene diisocyanate (2,7,7,9,15-pentamethyl-3,14-dioxa-4,13-dioxo-5,12-diazahexadecane 1,16-dioxydi(meth)acrylate CAS-No.: 105883-40-7), of 2 mol of hydroxypropyl(meth)acrylate (HPMA) with 2,4,4-trimethylhexamethylene diisocyanate (2,7,9,9,15-pentamethyl-3,14-dioxa-4,13-dioxo-5,12-diazahexadecane 1,16-dioxydi(meth)acrylate), of 2 mol of HPMA with 2,4-dimethylhexamethylene diisocyanate (2,7,9,15-tetramethyl-3,14-dioxa-4,13-dioxo-5,12-diazahexadecane 1,16-dioxydi(meth)acrylate), of 2 mol of HPMA with hexamethylene diisocyanate (2,15-dimethyl-3,14-dioxa-4,13-dioxo-5,12-diazahexadecane 1,16-dioxydi(meth)acrylate CAS-No.: 52723-94-1), of 2 mol of HPMA with isophorone diisocyanate (1,5,5-trimethyl-1-[(1-methacryloyloxypropan-2-yl)carbamoylmethyl]-3-(1-methacryloyloxypropan-2-yl)carbamoylcyclohexane CAS-No.: 76701-94-5), of 2 mol of HPMA with 2,2,4,4-tetramethylhexamethylene diisocyanate (2,7,7,9,9,15-hexamethyl-3,14-dioxa-4,13-dioxo-5,12-diazahexadecane 1,16-dioxydi(meth)acrylate), and the variants which can be produced by reaction of the abovementioned diisocyanates with hydroxyethylacrylate (HEA) and hydroxypropylacrylate (HPA).

The light-curable polysiloxanes, as the link between inorganic and organic chemistry, have exceptional material properties. Light-curable polysiloxanes are commonly known as constituents of dental composite materials by the "ormocers" name (organically modified ceramics). Cited here by way of example are DE 44 16 857 C1, DE 198 60 364 C2, EP 1 874 847 B1, EP 1 685 182 B1, WO 2013/041723 A1, WO 2013/053693 A1 or DE 10 2014 210 432. Since the light-curable polysiloxanes are physiologically inert, i.e. have no significant toxicity, they are especially important for applications in medicine. The basis for the near absence of toxicity of the polysiloxanes is the low biological assailability of the silicon-carbon bonds and the limited diffusion capacity of the strongly hydrophobic polymer chains through cell membranes, and for that reason they should be particularly suitable for implantation (in teeth).

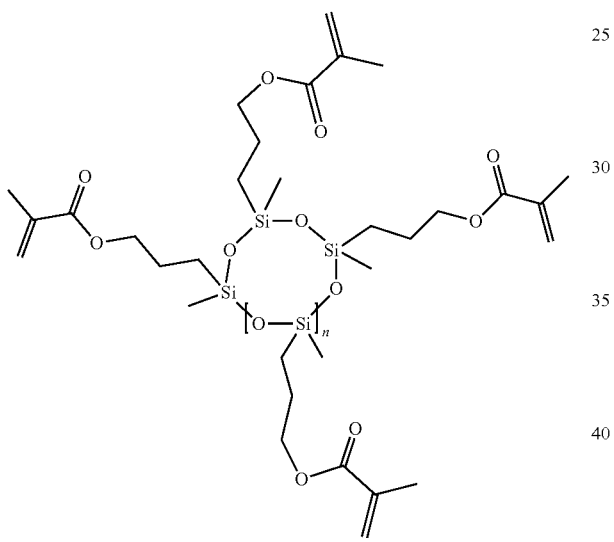

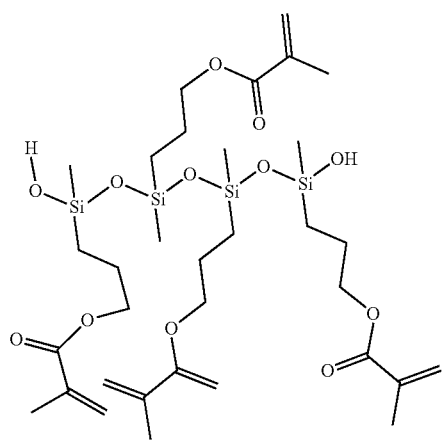

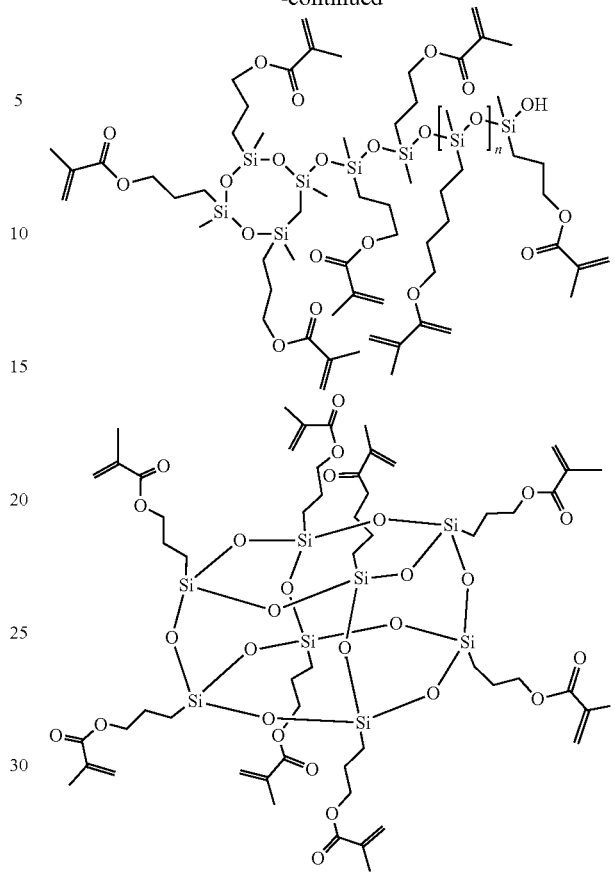

Polysiloxanes having at least 3 silicon atoms that are in chain-like and/or cyclic and/or cage-type form and have been substituted by free-radically polymerizable groups can be synthesized via the sol-gel method by controlled hydrolysis and condensation of correspondingly functionalized derivatives of alkoxides of silicon, or of halosilanes. These preparation methods have been described many times in the literature. In general, such a synthesis proceeds from a standard silane, for example isocyanatopropyldiethoxysilane, which is reacted in a first step, likewise in a standard reaction, for example in an isocyanate-alcohol polyaddition, for example with glycerol 1,3-dimethacrylate, to give the corresponding urethane. The compound obtained here consists on the one hand of the silicon atom furnished with hydrolysable and condensable groups, connected via what is called a spacer consisting of an alkyl group (a propyl group here) and a urethane group as structural connecting element to a further functional structural segment, in this case to two free-radically polymerizable methacrylate groups. Such a simple synthesis method can be modified in various ways since the possible reactions between correspondingly functionalized silanes and suitable reactants seem unlimited. The synthesis proposals in the literature are correspondingly extensive. The starting compound thus comprises an inorganically condensable structural element, a variable connecting element and a free-radically crosslinkable organic base skeleton. In a catalytically controlled hydrolysis and condensation, the polysiloxane is obtained as an inorganic condensate, substituted by free-radically polymerizable groups. Whether the polycondensate is in the form of chains, rings or three-dimensional cage forms, or in the corresponding mixed forms, depends on the exact conditions of the condensation. These include, as well as the reaction conditions (pH, amount of solvent and water, type and amount of catalyst, reaction temperature, type of workup, etc.), also the structural forms of the starting silane, significant factors being the number of alkoxy groups, the number of free-radically polymerizable groups, the chemical nature of the connecting element and the chain length of the spacer. Details of this can be found both in the scientific literature and in the patent literature.

The light-curable polysiloxane examined in this application was synthesized as follows: 100 g (0.42 mol) of 3-methacryloyloxypropyldimethoxymethylsilane are dissolved in 400 ml of ethyl acetate. 10 ml of 1N HCl solution are added dropwise and the mixture is stirred at 30° C. for 72 h. The mixture is extracted by shaking with 2N NaOH solution and washed with water, and the organic phase is dried over magnesium sulfate. After addition of BHT, the mixture is first concentrated by rotary evaporation at 40° C. and then solvent residues (e.g. water and alcohol residues) are drawn off under reduced pressure by means of an oil pump in order to remove the alcohol and water residues. The result is a liquid resin having a viscosity of 3 Pa*s at 25° C. $n_D^{20}=1.466$ The term "light-curable polysiloxanes" describes the compounds of alkoxides of silicon or of halosilanes that have been functionalized with light-curable groups, where the light-curable groups are unsaturated hydrocarbyl groups, for example $—CH=CH_2$, $—C(CH_3)=CH_2$, $—CH_2—CH=CH_2$, $—CH_2—C(CH_3)=CH_2$ and $—O—CH=CH_2$, preferably unsaturated activated hydrocarbyl groups, for example $—O—(C=O)—CH=CH_2$ and $—O—(C=O)—C(CH_3)=CH_2$ or $—(C=O)—CH=CH_2$, $—(C=O)—C(CH_3)=CH_2$.

In a preferred light-curable mixture according to the invention, component (A5) is present in a proportion of less than 10% by weight, preferably of less than 5% by weight, based on the total mass of the monomers (A).

In a particularly preferred light-curable mixture according to the invention, the optional constituent (A5) is absent.

The dental, light-curable, one-component, composite composition according to the invention contains fillers (B) in an amount of 65% to 93% by weight, based on the composite composition.

The remarks relating to fillers (B) usable in accordance with the invention are applicable both to the use of the fillers in the dental, light-curable, one-component composite compositions according to the invention and to use in the methods according to the invention. In particular, fillers usable with preference in dental, light-curable, one-component composite compositions according to the invention are also usable with preference in the methods according to the invention, and vice versa.

In a preferred embodiment, the fillers (B) consist of and/or are producible by mixing (B1) 2% to 25% by weight, preferably 3% to 20% by weight, of inorganic filler having a $D_{50}$ of 1 nm to 200 nm, and further filler constituents, preferably (B2) 40% to 90% by weight, preferably 50% to 80% by weight, of inorganic filler having a $D_{50}$ of greater than 1 µm to 10 µm, (B3) 8% to 50% by weight, preferably 15% to 40% by weight, of inorganic filler having a $D_{50}$ of 0.4 µm to 1.0 µm and (B4) 0% to 25% by weight, preferably 0% to 15% by weight, of further fillers that cannot be assigned to (B1), (B2) or (B3), wherein the percentages by weight of (B1), (B2), (B3) and (B4) are based on the total mass of the fillers (B).

The filler component (B1) is particularly important, especially in order to establish the viscosities of $\eta_{20}$ and $\eta_{50}$ at a high filler content of greater than 75% by weight.

(B1) are nanoscale oxides or mixed oxides within the size range below 200 nm, preferably below 100 nm and more preferably below 70 nm, which are selected from the group consisting of the elements silicon, titanium, yttrium, barium, zirconium, hafnium, niobium, tantalum, tungsten, bismuth, molybdenum, tin, zinc, ytterbium, lanthanum, cerium, aluminium and mixtures thereof.

Particular preference is given to nanoscale particles of $SiO_2$, $TiO_2$, $ZrO_2$, $ZnO$, $SnO_2$ and $Al_2O_3$ and mixtures thereof.

(B1) may likewise be nanoscale sulfides, selenides and tellurides of metals, mixed metals and mixtures thereof within the size range below 200 nm, preferably below 100 nm and more preferably below 70 nm.

In order to assure good binding of the nanoparticles into the organic phase of the dental, light-curable, one-component composite material according to the invention, the surfaces of the nanoparticles have been organically modified, meaning that their surfaces have organic structural elements.

Suitable compounds for organic surface modification are preferably those of the general X-Sp-V type where "X" and "V" denote functional groups connected to one another by a linker (spacer, "Sp").

The functional "X" group is preferably selected such that it can enter into a corresponding bond to the surface of the filler particle with complex formation. Suitable examples are groups of the silane, phosphate, phosphonate, carboxylate, dithiophosphate, dithiophosphonate, amine and amide type. The surface binding of the compound to the filler particles for an organic surface modification can be improved by replication of a functional group (polyphosphates, polycarboxylates).

Suitable linkers (spacers, "Sp") are linear or branched alkyl chains, aromatic systems or combinations of these groups that may each be interrupted by heteroatoms such as O, N, S or P or by a urethane group.

The functional "V" group mediates the compatibility of the filler particles with the total amount of the light-curable monomers (A), for example by hydrophobization. Preference is given to light-curable groups; preference is given here to linear or branched alkyl, arenyl or alkenyl groups, the latter offering the advantage of being incorporated into the polymerization of the curable monomers, which leads to good incorporation of the particles into the cured dental material. In this context, particular preference is given to (meth)acrylate groups.

In a preferred form, the oxidic nanoscale fillers are nanoscale silicas. The nanoscale silicas are prepared in a known manner, for example by flame pyrolysis, plasma methods, gas phase condensation, colloidal techniques, precipitation methods, sol-gel methods, etc.

The nanoscale silicas that can be used in dental, light-curable, one-component composite compositions according to the invention are also commercially available, for example under the "NALCO COLLOIDAL SILICAS" (Nalco Chemical Co.), "Ludox colloidal silica" (Grace) or "Highlink OG" (Clariant) trade name.

In a particularly preferred manner, the silicas are surface-treated using silanes. A particularly suitable adhesion promoter is methacryloyloxypropyltrimethoxysilane. Compounds of the formula (1) or (2) are particularly preferred for the silanization.

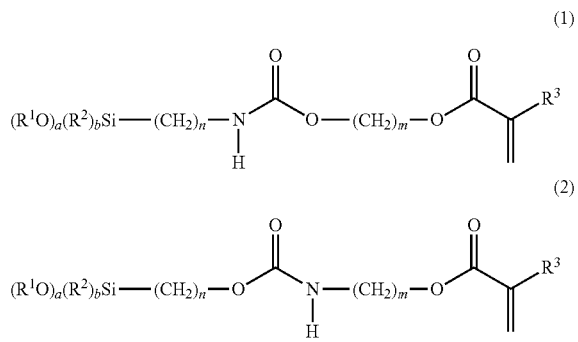

wherein $R^1$ denotes a C1- to C4-alkyl group, and
$R^2$ denotes a C1- to C8-alkyl group, and
$R^3$ denotes a hydrogen atom or a methyl group, and
a=1, 2 or 3, and
b=3−a, and
n=1 to 8, and
m=1 to 8.

The method of preparation of silanized filler surfaces involves first adjusting an ethanol/water mixture (usually 95/5% by volume) to a pH of 4.5-5.5 with acetic acid. The silane is then added in such an amount as to result in a solution concentration of about 2%. Within 5 minutes, the alkoxysilyl groups have been hydrolysed and siloxane formation sets in. Then the filler to be treated is added to the solution with continued stirring. Within a few minutes, the silane is adsorbed by the filler and the surface of the filler material is laden with the adhesion promoter. The solution is decanted off and the particles are washed twice with ethanol. Finally, the residual silanol functions are condensed at 110° C. for a few minutes and at room temperature for 24 hours.

The silane acts as a surfactant that compatibilizes the surface of the filler with the resin matrix and ensures a strong bond between the organic material and the inorganic material.

Particularly suitable silanes to form a bond between the inorganic phase and the organic phase have been found to include 3-methacryloyloxypropyltrimethoxysilane and more preferably the silanes of the formulae (1) and (2). Some of the hydrolysed alkoxysilyl groups of the silane react directly with the hydroxyl groups on the mineral surface of the filler, while the rest are condensed with one another and thus result in a coherent layer of the coupling reagent on the filler surface. In the course of the later free-radical polymerization of the dental composite material, the methacryloyl functions of the continuous layer of the silane adhering to the filler surface are then also polymerized into the organic resin phase and hence form a permanent bond between the hydrophilic fillers and the hydrophobic resin matrix.

As well as the nanoscale oxides and/or mixed oxides and the abovementioned metal salts, component (B-1) also includes the x-ray-opaque nanoscale salts within the size range below 200 nm, preferably below 100 nm and more preferably below 70 nm of the rare earths (elements 57-71), of scandium and of yttrium. The preferred lanthanoids include lanthanum, cerium, samarium, gadolinium, dysprosium, erbium and ytterbium. Among the salts thereof, preference is given to the fluorides, especially nanoscale ytterbium fluoride ($YbF_3$).

The x-ray-opaque salts also include particular nanoscale salts of the alkaline earth metals within the size range below 200 nm, preferably below 100 nm and more preferably below 70 nm, for example the salts of barium and strontium. Preferred salts from this group are fluorides, phosphates and sulfates, especially nanoscale barium sulfate ($BaSO_4$) and nanoscale strontium fluoride ($SrF_2$).

For surface treatment of the x-ray-opaque nanoscale salts within the size range below 200 nm, preferably below 100 nm and more preferably below 70 nm, especially of ytterbium fluoride, of strontium fluoride and of the mixed fluorides such as strontium-doped ytterbium fluoride particles and of barium sulfate, in a particularly preferred manner, phosphates, phosphonates or carboxylates are used, where the bonding agent is bonded to a (meth)acrylate group via a spacer.

Of the x-ray-opaque salts, particular preference is given in accordance with the invention to ytterbium fluoride, strontium fluoride, barium sulfate and the mixed fluorides between ytterbium fluoride and strontium fluoride, very particular preference being given in accordance with the invention to strontium fluoride-doped ytterbium fluoride and/or ytterbium fluoride-doped strontium fluoride.

The nanoparticles (B1) are preferably non-agglomerated and non-aggregated. In that case, they are dispersed in a medium, preferably in monodisperse form.

Inorganic non-nanoscale fillers (B2) and (B3) within the size range above 200 nm, within the range referred to hereinafter as "microscale", that may be used are compact glasses and differently agglomerated and aggregated silicas in various sizes and states (monodisperse, polydisperse).

Suitable inorganic microscale constituents (B2) and (B3) are, for example, amorphous materials based on oxides or mixed oxides of $SiO_2$, $ZrO_2$ and/or $TiO_2$ and fillers such as quartz glass ceramic or glass powders, barium silicate glasses, barium fluorosilicate glasses, strontium silicate glasses, strontium borosilicates, Li/Al silicate glasses, barium glasses, calcium silicates, sodium aluminium silicates, fluoroaluminium silicate glasses, oxides of aluminium or silicon, zeolites, apatite, zirconium silicates, sparingly soluble metal salts such as microscale barium sulfate or calcium fluoride, and x-ray-opaque fillers such as microscale ytterbium fluoride.

For better incorporation into the polymer matrix, the microscale fillers may also have been organically surface-modified. Examples include the surface treatment of the fillers with a silane. A suitable adhesion promoter here is particularly methacryloyloxypropyltrimethoxysilane. Here too, particular preference is given to using the silanes of the formulae (1) and (2).

Within a light-curable, one-component dental composition according to the invention, the microparticles bring about largely homogeneous filling of the volume, with at least partial filling of the remaining voids between the microparticles by the above-described nanoparticles (component (B1)). Microparticles in connection with the present invention are understood to mean particles having an average particle size of more than 200 nm to 10 μm. The average particle size is preferably less than 5 μm. It has been found that the smaller the microparticles, the more complete and homogeneous the filling of volume of the light-curable, one-component dental composition already achievable by the microparticles.

This reduces both the shrinkage of the dental composition and its sensitivity to abrasion.

The microparticles of the respective components (B2) and (B3) may have a monomodal or polymodal particle size distribution, for example a bimodal particle size distribution. Preference is given in accordance with the invention to the total microparticle fraction with a bimodal or multimodal particle size distribution (in that case with a monomodal particle size distribution of the respective microparticle components (B2) and (B3)), since more complete filling of volume is achievable therewith than in the case of general use of microparticles having monomodal particle size distribution. In the presence of a bi- or multimodal particle size distribution, the particles in the fractions with the greater particle size bring about coarse filling of the volume, while the particles of the fraction with the smaller particle size, as far as possible, fill the regions between the particles of the fractions with the greater particle size. The voids still remaining are filled by nanoparticles as described above.

Thus, very particular preference is given to using, in a light-curable, one-component dental composition according to the invention, a total microparticle component ((B2) plus (B3)) comprising two or more fractions of microparticles, where there is a difference in the average particle sizes of the fractions.

Preferably, the total microscale component ((B2) plus (B3)) comprises at least two microparticle fractions, where the average particle sizes thereof differ from one another by at least 0.5 µm, preferably by at least 0.7 µm. In some configurations, the difference in the average particle sizes of the microparticle fractions is at least 1.0 µm.

The microparticles of different fractions may consist of the same or different materials; there may also be multiple fractions of microparticles, the average particle size of which is virtually the same or within a certain range, wherein the materials of the particles differ between the fractions.

More preferably, a light-curable, one-component dental composition according to the invention comprises a total micro component ((B2) plus (B3)) having a first microparticle fraction (B2) in each case having an average particle size in the range from 1 µm to 10 µm, preferably from 1.2 µm to 5 µm and more preferably from 1.5 µm to 4.0 µm, and a second microparticle fraction (B3) in each case having an average particle size in the range from 0.4 µm to 1 µm, preferably from 0.5 µm to 0.9 µm and more preferably from 0.6 µm to 0.8 µm.

Preferably, the ratio of the total mass of (B2) to (B3) is in the range from 1:1 to 12:1, preferably in the range from 1.5:1 to 8:1.

Preferably, the ratio of the average particle size of (B2) to the average particle size of (B3) is in the range from 1.5:1 to 10:1, preferably in the range from 2:1 to 5:1.

In a particularly preferred light-curable, one-component dental composition according to the invention, component (B) comprises a first microparticle fraction (B2) in each case having an average particle size in the range from 1 µm to 10 µm, preferably 1.2 µm to 5 µm and more preferably 1.5 µm to 4.0 µm, and a second microparticle fraction (B3) in each case having an average particle size in the range from 0.4 µm to 1 µm, preferably from 0.5 µm to 0.9 µm and more preferably from 0.6 µm to 0.8 µm; wherein the ratio of the total mass of the first microparticle fraction to the total mass of the second microparticle fraction is in the range from 1:1 to 12:1, preferably 1.5:1 to 8:1, and/or the ratio of the average particle size of the first microparticle fraction (B2) to the average particle size of the second microparticle fraction (B3) is in the range from 1.5:1 to 10:1, preferably 2:1 to 5:1.

In a particularly preferred light-curable, one-component dental composition according to the invention, at least some of the microparticles of components (B2) and (B3) are formed by organically surface-modified particles, preferably silanized particles, and/or at least some of the microparticles of components (B2) and (B3) are formed by dental glass particles; preferably, at least some of the microparticles of components (B2) and (B3) are organically surface-modified dental glass particles, preferably silanized dental glass particles.

As well as components (B1), (B2) and (B3), the light-curable, one-component dental composition, in addition to the mixture of filler particles, may comprise further fillers as component (B4).

For example, it is possible to use reinforcing filler materials, such as glass fibres, polyamide fibres or carbon fibres. A light-curable, one-component dental composition according to the invention may also contain fine and/or coarse inorganic fillers in particle sizes different from those of (B2) and (B3), and also splinter or bead polymers, where the bead polymers may be homo- or copolymers of organically curable monomers.

A light-curable, one-component dental composition according to the invention may also including microscale x-ray-opaque filler. In that case, the composition according to the invention contains microscale $YbF_3$ and/or $BaSO_4$.

Qualitative and quantitative characterization of the filler particles:

The steps described hereinafter in the qualitative and quantitative characterization of the filler particles (especially of nanoscale filler particles) are well known to the person skilled in the art and described extensively in the literature.

Resin/Filler Separation:

In a first step, 1 g of a light-curable, one-component dental composition according to the invention (hereinafter referred to as composite material) is resuspended in 10 ml of acetone, and the suspension obtained is then centrifuged with a centrifuge at 5000 rpm for 10 min. The supernatant (called resin phase hereinafter) is decanted off into a collection bottle and the residue is slurried in 5 ml of acetone. The slurry is centrifuged again at 5000 rpm for 10 min and decanted, and the residue is slurried again in 5 ml of acetone. The steps of centrifuging, decanting and slurrying are repeated twice more under identical conditions. The total amount of residues separated from the resin phases is dried, and the acetone is removed from the total amount of resin phases on a rotary evaporator.

After the first step has been performed, the dried total amount of residues regularly comprises those filler particles that have a particle size of 200 nm or greater 200 nm (hereinafter referred to as macroscopic filler particles). The total amount of resin phases that has been freed of acetone (hereinafter referred to as resin fraction) comprises, as well as polymerizable monomers, regularly also filler particles having a particle size of about 200 nm or especially less than 200 nm (hereinafter referred to as nanoscale particles). This method thus ensures that the dental composite material is separated completely by the centrifugation into (i) a fraction of macroscopic filler particles, relating specifically to the dental glasses within the size range of the order of greater than 200 nm up to the high micrometer range, and (ii) a resin fraction comprising nanoscale particles.

The median particle size $d_{50}$ of the macroscopic filler particles for use in accordance with the invention of filler components (B2), (B3) and (B4) of a composition according to the invention is determined by means of light scattering (laser diffraction), preferably with a Beckman Coulter LS 13320 particle size analyser.

The nanoscale particles present in the resin fraction may, for example, be either non-aggregated and/or non-agglomerated particles, for example including x-ray-opaque particles, for example $YbF_3$ or $BaSO_4$ having particle sizes within a range from about 3 nm to 200 nm, preferably from 5 nm to 200 nm, more preferably from 7 nm to 100 nm and most preferably from 7 nm to 70 nm, or non-x-ray-opaque silicas that are synthesized, for example, in the form of fumed silicas in the form of aggregates and/or agglomerates having a particle size within a range from about 150 nm to about 200 nm or else silicas which are synthesized by the sol-gel method (or else from waterglass) and which are likewise in non-aggregated and/or non-agglomerated form and have particle sizes within a range from about 3 nm to 200 nm, preferably from 5 nm to 200 nm, more preferably from 7 nm to 100 nm and most preferably from 7 nm to 70 nm.

The total proportion by mass of inorganic particles in the resin component is determined gravimetrically by differential weighing after ashing of a corresponding resin component.

TEM in Combination with EELS:

In a second step, the filler particles in the resin component are subjected to qualitative and quantitative characterization. For this purpose, TEM (transmission electron microscopy) is used in conjunction with EELS (electron energy loss spectroscopy).

By means of TEM, the particle size of the individual particles and the number thereof are determined; elemental determination of individual particles is effected by means of EELS.

For performance of the combined TEM/EELS characterization, in a first step, the concentration of the nanoscale particles in the resin fraction is first reduced by dilution with curable resin. This very substantially rules out observation of "overlapping" of nanoscale particles in the later images. Such "overlapping" would distort the particle characterization. In-house studies have shown that the optimal particle concentration (i.e. the proportion by volume of the filler particles) for such studies is 1% by volume, based on the total mass of the diluted sample.

In a second step, the diluted resin fractions obtained by dilution with curable resin are used to produce bar specimens by curing. These bar specimens are used to produce multiple 300 nm ultrathin sections with an ultra diamond blade (for example ULTRCAT UCT ultramicrotome, LEICA, Wetzlar). For stabilization, the ultrathin sections are transferred to copper TEM grids. This results in thin-layer preparations. These thin-layer preparations are then analysed at acceleration voltage 120 kV in a TEM by means of bright-field images.

A TEM analysis on the above-described thin-layer preparations permits distinction of non-aggregated and non-agglomerated nanoscale particles from aggregated and/or agglomerated particles (e.g. silicas, for example aerosils) (for identification of the chemical composition see the remarks which follow).

If high-resolution images are to be examined, ultrathin sections with layer thicknesses less than 100 nm may be produced and analysed.

In a third step, the filler particles in the ultrathin sections or thin-layer preparations are chemically characterized by means of EELS spot analyses, such that the chemical composition of individual particles becomes known (for determination of the surface modification of particles see points which follow).

The proportions of (possibly even multiple) particle fractions based on volume or weight are determined in a fourth step from a TEM image as follows: the image section of a TEM image viewed in a microscope constitutes an area, the edge lengths a and b of which are determined by means of the legend. Multiplied by the thickness c of the ultrathin section, this results in a total volume $V_{total}$ for the TEM region under consideration. This total volume $V_{total}$ is the sum total of the resin volume $V_{resin}$ and the volume of all particles $V_{particles}$ within this volume (the volume of all particles includes possibly multiple groups of particles, sorted, for example by various criteria, for example size). The following equation applies: $V_{total}=a*b*c=V_{resin}+V_{particles}$.

The volume of individual particles (and hence the volume of all the particles in the volume under consideration) is obtainable by calculation via the sphere volume of the individual particles. For this purpose, in the TEM image, the diameter or radius of an appropriate particle is determined. The sphere volume calculated therefrom, multiplied by the density of the corresponding material of which the particle consists (material identifiable by means of EELS), gives the mass of the particle. The resin volume, obtainable from the total volume minus the particle volume, multiplied by the resin density, gives the resin mass. The resin density is found very substantially from the density of the resin used for dilution and, if appropriate, the density of the diluted resin fraction (the latter can possibly be neglected in the calculation of the resin density if the proportion of the diluted resin is negligible). The proportion of the particles (or a group of particles) in percent by weight is calculated from $m_p*100/(m_{particles}+m_{resin})$ where $m_p$ is the mass of the particle fraction under consideration in the volume under consideration, $m_{particles}$ is the mass of all the particles in the volume under consideration and $m_{resin}$ is the mass of the resin in the volume under consideration. In the final calculation of the proportion by weight of the particle fraction under consideration, the dilution factor is taken into account appropriately.

Determination of Organic Surface Modifications:

Preliminary Assessment:

Many known x-ray-opaque filler materials (for example ytterbium fluoride or barium sulfate) have the disadvantage that they can be incorporated only with difficulty into the matrix (resin matrix) composed of polymerizable monomers (called the organic resin phase) because they do not enter into sufficient chemical bonds (binding opportunities) with the hydrophobic groups of the medium. Vitreous fillers can be incorporated in an excellent manner into the resin matrix of dental composite materials, for example, with the aid of silanization via Si—OH groups. In the case of ytterbium fluoride and barium sulfate, no such groups are present on the surfaces; they are therefore not silanizable and lead to inadequate physical and chemical resistance in a cured dental material (see WO 2005/011621 A1, bottom of page 2).

The x-ray-opaque nanoscale particles used in a light curable, one-component dental composition according to the invention will therefore not have any silanes on their surfaces. Instead, the linking is effected via nitrogen, oxygen, sulfur and/or phosphorus atoms (again, see WO 2005/011621 A1 and our remarks further up in the text).

Removal of Polymerizable Monomers from Nanoscale Particles:

"Cross-Flow" Method:

The removal of polymerizable monomers from nanoscale particles is effected, for example, in a "cross-flow" method known to those skilled in the art by means of ultrafiltration membranes.

In this method, a resin fraction comprising nanoscale particles, polymerizable monomers and optionally a suitable diluent is pumped from a vessel by means of a pump into a circuit composed of particular membranes, and the polymerizable monomers pass through the pores of the membranes and are separated as filtrate, while the nanoscale particles remain within the circuit (and hence within the vessel).

An example of a suitable system for this separating step is the "Vivaflow 50" system from "Sartorius Stedim Biotech GmbH, Gottingen". The pump drive (7554-95) and pump head come from the "Masterflex L/S" series from "Cole Parmer Instrument Co.", Illinois, USA. The operation of the pump is set to 2.5 bar during the filtration. Two separation membranes of the "50,000 MWCO (PES)" type are connected in series. The MWCO (molecular weight cutoff) defines the separation limit here, i.e. the size of the molecules which can still pass efficiently through the membrane. This value is reported in daltons. The fractions obtained are subsequently analysed as described below.

Sedimentation Field-Flow Fractionation (SF3):

Even better than the "cross-flow" method is the performance of a sedimentation field-flow fractionation (SF3). This can especially separate different particle fractions from one another and additionally from the resin component. It is a prerequisite here that the different particle fractions differ sufficiently from one another in terms of size and/or density.

Corresponding equipment containing a separation column necessary for the purpose is obtainable from Postnova Analytics GmbH, Landsberg. The module containing the separation column is identified as CF2000 Centrifugal FFF and is supplemented by the further modules PN7140 (Eluent Organizer), PN1130 (Isocratic Pump), PN5300 (Autosampler), PN3621 MALS (21-Multi-Angle Light Scattering Detector) and PN8050 (Fraction Collector). In this combination, the Centrifugal FFF system allows not just the analytical but also the preparative separation of particle fractions. The fractions obtained are subsequently analysed as described below.

Characterization of the Surface Modification:

A sample which has been produced as above and then freed of solvents, containing nanoscale particles in the form of a powder, is subsequently examined by means of spectroscopic methods (for example by means of $^1$H NMR, $^{13}$C NMR, $^{15}$N NMR, $^{29}$Si NMR and $^{31}$P NMR, and also IR).

Signals which cannot be attributed to a silane, for example the gamma-methacryloyloxypropylsilyl radical, are attributed to organic surface modifications not based on silanes, for example surface modifications by means of organic compounds on surfaces of ytterbium fluoride or barium sulfate particles.

The proportions of organically surface-modified particles and/or non-organically surface-modified particles can also be determined regularly by evaluation of the intensities of corresponding vibration bands in the IR spectrum. For this purpose, reference vibration bands (reference curves) of organically surface-modified or non-organically surface-modified particles with the corresponding chemical compositions are conventionally employed.

Characterization by Means of Image Analysis and Raman Spectroscopy:

The person skilled in the art is aware of additional methods and coupled methods which allow qualitative and quantitative characterization of the filler particles. In this respect, reference is made, for example, to the article "Chemische Identitat einzelner Partikel" [Chemical Identity of Individual Particles] by Deborah Huck-Jones and Renate Hessemann in "Nachrichten aus der Chemie", Volume 62, September 2014, pages 886 and 887. The combination of image analysis and Raman spectroscopy disclosed therein is regularly also suitable for characterization of the filler particles in the context of the present invention. This applies in particular to samples which are obtained by the resin/filler separation described above. An example of a suitable image analysis is again the TEM analysis described in the text above.

Constituent (C)—Initiators and/or Catalysts for Free-Radical Polymerization

A light-curable, one-component dental composition according to the invention contains initiators and/or catalysts for free-radical polymerization, wherein constituent (C) comprises or consists of one or more light curing initiators.

The remarks relating to the initiators usable in accordance with the invention relate both to the use of the initiators in the dental, light-curable, one-component composite compositions according to the invention and to use in the methods according to the invention. More particularly, initiators usable with preference in dental, light-curable, one-component composite compositions according to the invention are also usable with preference in the methods according to the invention, and vice versa.

Examples of a light curing initiator include substances that have merely photosensitizing action, and combinations of sensitizer and accelerator.

Examples of photosensitizers are alpha-diketones, benzoin alkyl ethers, thioxanthones, benzophenones, acylphosphine oxides, acylgermanium compounds, acetophenones, ketals, titanocenes, sensitizing dyes, etc. The sensitizers can be employed alone or in combination. Specific substance examples from the different classes can be found, for example, in DE 10 2006 019 092 A1, or in DE 39 41 629 C2.

Examples of accelerators which are used together with the sensitizers are tertiary amines, secondary amines, barbituric acids, tin compounds, aldehydes and sulfur compounds. Specific substance examples from the different classes can be found in DE 10 2006 019 092 or in DE 39 41 629 C2.

Further suitable initiators and initiator combinations are described in DE 601 16 142.

The photoinitiators usable in the context of the present invention are characterized in that they can initiate the curing of a light-curable, one-component dental composition according to the invention by absorption of light within the wavelength range from 300 nm to 700 nm, preferably from 350 nm to 600 nm and more preferably from 380 nm to 500 nm, optionally in combination with one or more co-initiators.

The absorption maximum of camphorquinone (CQ) is at about 470 nm and is therefore within the blue light range. Camphorquinone (CQ) is one of the $PI_2$ initiators and is regularly used together with a co-initiator.

Preferably, a composite material according to the invention contains the combination of an alpha-diketone and an aromatic tertiary amine, preference being given to the combination of camphorquinone (CQ) and ethyl p-N,N-dimethylaminobenzoate (DABE).

Likewise preferable is the further combination of the "alpha-diketone/aromatic tertiary amine" system with a phosphine oxide, especially with phenyl bis(2,4,6-trimethylbenzoyl)phosphine oxide and/or 2,4,6-trimethylbenzoyldiphenylphosphine oxide.

With regard to the structures of suitable phosphine oxides for use in a light-curable, one-component dental composition according to the invention, reference is made to publications DE3801511C2, DE102006050153A1, EP0184095B1, DE4231579C2, EP 0 366 977 B1, U.S. Pat. No. 7,081,485 B2, DE 32 36 026 A1, US 2007/0027229 A1, EP 0 262 629 B1, EP 0 073 413, U.S. Pat. No. 7,148,382 B2, U.S. Pat. No. 5,761,169, DE 197 08 294 A1, EP 0 057 474, EP 0 047 902 A, EP 0 007 508, DE 600 29 481 T2, EP 0 980 682 B1, EP 0 948 955 B1, EP 1 236 459 B1 and EP 0 173 567 A2.

The phosphine oxides specified in these publications are suitable particularly alone or in combination with the "alpha-diketone/amine" system as photopolymerization initiator system in a light-curable, one-component dental composition according to the invention.

EP 1 905 415 describes polymerizable dental compositions comprising acylgermanium compounds as initiators.

Alternatively, it is also possible to use borate salts, as described, for example, in U.S. Pat. Nos. 4,772,530, 4,954,414, 4,874,450, 5,055,372 and 5,057,393, as photoinitiators.

Further suitable photoinitiators are described in J.-P. Fouassier, Photoinitiation, Photopolymerization and Photocuring, Hanser Publishers, Munich, Vienna, New York 1995, and in J. F. Rabek (ed.), Radiation Curing in Polymer Science and Technology, Vol. II, Elsevier Applied Science, London, New York 1993.

Constituent (D)—Further Customary Additives

A light-curable, one-component dental composition according to the invention, in some cases, comprises one or more further additive(s).

The remarks relating to the additives usable in accordance with the invention relate both to the use of the additives in the dental, light-curable, one-component composite compositions according to the invention and to use in the methods according to the invention. More particularly, additives usable with preference in dental, light-curable, one-component composite compositions according to the invention are also usable with preference in the methods according to the invention, and vice versa.

These additives may have various functions. Customary additives for use in dental materials are known to the person skilled in the art; he or she will select the suitable additive(s) according to the desired function. Typical additives and their functions are described by way of example hereinafter.

Light-curable, one-component dental compositions as preferred in accordance with the invention preferably contain one or more inhibitor(s), also called stabilizer(s). These are typically added in order to prevent spontaneous polymerization. They react with free radicals formed prematurely, which are scavenged, prevent premature polymerization and increase the storage stability of the light-curable, one-component dental composition. Standard inhibitors are phenol derivatives such as hydroquinone monomethyl ether (HQME) or 2,6-di-tert-butyl-4-methylphenol (BHT). Further inhibitors such as tert-butylhydroxyanisole (BHA), 2,2-diphenyl-1-picrylhydrazyl radicals, galvinoxyl radicals, triphenylmethyl radicals, 2,3,6,6-tetramethylpiperidinyl-1-oxyl radicals (TEMPO), and derivatives of TEMPO or phenothiazine and derivatives of this compound are described in EP 0 783 880 B1. Alternative inhibitors are specified in DE 101 19 831 A1 or in EP 1 563 821 A1.

A light-curable, one-component dental composition preferred in accordance with the invention thus comprises, as additive, one or more polymerization inhibitors for increasing the storage stability of the composition, preferably selected from the group consisting of hydroquinone monomethyl ether (HQME), phenols, preferably 2,6-di-tert-butyl-4-methylphenol (BHT) and tert-butylhydroxyanisole (BHA), 2,2-diphenyl-1-picrylhydrazyl radicals, galvinoxyl radicals, triphenylmethyl radicals, 2,3,6,6-tetramethylpiperidinyl-1-oxyl radical (TEMPO) and derivatives thereof, and phenothiazine and derivatives thereof.

A light-curable, one-component dental composition according to the invention may comprise, as additive, one or more fluoride-releasing substances, preferably sodium fluoride and/or amine fluorides.

UV absorbers which are capable of absorbing UV radiation, for example, by virtue of their conjugated double bond systems and aromatic rings are in some cases part of a light-curable, one-component dental composition according to the invention. Examples of UV absorbers are 2-hydroxy-4-methoxybenzophenone, phenyl salicylate, 3-(2'-hydroxy-5'-methylphenyl)benzotriazole or diethyl 2,5-dihydroxyterephthalate.

Since the teeth should be restored as realistically as possible, it is necessary to provide light-curable, one-component dental compositions according to the invention in a wide variety of different shades. For this purpose, generally inorganic dyes and organic pigments are utilized in very small amounts, which are thus used as additive in preferred configurations.

Further optional additives are aromas, dental medicaments, organic polymers and oligomers, preferably plasticizers, microbicides, preferably bactericides, interface-active substances, preferably surfactants, preservatives or molecular weight regulators.

The invention likewise encompasses a cured composite composition which is obtained by light curing of a dental, light-curable, one-component composite composition according to the invention.

The invention also encompasses a dental, light-curable, one-component composite composition according to the invention for use in a method of dental treatment, preferably for use in a method of dental treatment having the following steps:
- heating the composite composition to a temperature of 40° C. or more, preferably a temperature in the range from 40° C. to 80° C., preferably in an oven and/or by irradiation, preferably with IR rays,
- contacting the composite composition that has been heated to a temperature of 40° C. or more, preferably a temperature in the range from 40° C. to 80° C., with a patient's tooth to be treated, preferably as dental filling material, lining material, luting material and fissure sealant.

The invention is additionally directed to the use of a composite composition according to the invention for production of a dental product, wherein the production is not effected on the human or animal body.

In a particular embodiment, the invention likewise relates to a device for application of a composite composition according to the invention, comprising
- a cavity filled at least partly with an amount of a composite composition and
- an application tip connected to the cavity and having an exit opening for the composite composition.

In a further particular embodiment, the invention also relates to a device as described above, wherein the exit opening has a cross-sectional exit area in the range from 0.2 to 3.0 mm$^2$, preferably a cross-sectional exit area of not more than 2.0 mm², more preferably a cross-sectional exit area of not more than 1.5 mm², and wherein the application tip of the device is a cannula preferably consisting of metal or plastic and/or the device is selected from the group consisting of compules and syringes.

In the case of large cross-sectional exit areas of the devices according to the invention, the composite composition according to the invention, due to its sufficiently high viscosity at room temperature, allows drip-proof storage and handling of the filled device, and hence avoidance of contamination of working surfaces. At the same time, its sufficiently low viscosity on heating (for example to 40° C. to 80° C.) also allows configuration of the device with a minimum cross-sectional exit area in order to assure precise application during treatment.

The invention is additionally directed to a method of producing a composite composition according to the invention or for producing a device for application of a composite composition according to the invention, having the following step:

mixing the components (A) monomers in an amount of 6% to 35% by weight, based on the total amount of the composite composition, preferably 10% to 35% by weight, more preferably 10% to 25% by weight, (B) fillers in an amount of 65% to 93% by weight, preferably 65% to 89% by weight, more preferably 75% to 89% by weight, based on the total amount of the composite composition, (C) initiators in an amount of 0.001% to 3% by weight based on the total amount of the composite composition, (D) further additives in an amount of 0.001% to 5% by weight based on the total amount of the composite composition, to give the composite composition, wherein the components are selected such that the viscosity $\eta_{20}$ of the composite composition at 20° C. is greater than 400 Pa*s and the viscosity $\eta_{50}$ of the composite composition at 50° C. is less than 150 Pa*s and wherein the quotient $\eta_{50}/\eta_{20}$ of the viscosity of the composite composition at 50° C. and the viscosity of the composite composition at 20° C. is less than 0.125, preferably less than 0.1.

Preference is given to a method according to the invention wherein component (A) is produced by the following steps:

providing at least (A-i) one first monomer substance and (A-ii) one second monomer substance, wherein the viscosity $\eta_{20}$ of the second monomer substance (A-ii) at 20° C. is greater than 100 Pa*s, the viscosity $\eta_{20}$ of the first monomer substance (A-i) at 20° C. is greater than 100 mPa*s, the viscosity of the second monomer substance (A-ii) at 20° C. is greater than that of the first monomer substance (A-i)

and the mass ratio of the first monomer substance (A-i) to the second monomer substance (A-ii) is in the range from 2:1 to 1:10, wherein the second monomer substance (A-ii) preferably contains at least 40% by weight of 2,2-bis[4-(2-hydroxy-3-methacryloyloxypropoxy)phenyl]propane (bis-GMA) and/or light-curable derivatives of diisocyanatodiphenylmethane (MDI) and/or light-curable derivatives of tetramethyl-m-xylylene diisocyanate (TMXDI), wherein the percentage by weight is based on the total mass of the monomers (A), and mixing the monomer substances (A-i) and (A-ii) provided, prior to the and/or in the course of mixing with constituents (B), (C) and (D), and/or wherein constituent (B) is produced by mixing (B1) 2% to 25% by weight, preferably 3% to 20% by weight, of inorganic filler having a $D_{50}$ of 1 nm to 200 nm, and further filler constituents, preferably (B2) 40% to 90% by weight, preferably 50% to 80% by weight, of inorganic filler having a $D_{50}$ of greater than 1 μm to 10 μm, (B3) 8% to 50% by weight, preferably 15% to 40% by weight, of inorganic filler in a size having a $D_{50}$ of 0.4 μm to 1.0 μm and (B4) 0% to 25% by weight, preferably 0% to 15% by weight, of further fillers that cannot be assigned to (B1), (B2) or (B3), wherein the percentages by weight of (B1), (B2), (B3) and (B4) are based on the total mass of the fillers (B).

Particular preference is given to a method according to the invention having the following additional step for preparation of the device for application of a composite composition: introducing the composite composition according to the invention that has been produced into a cavity of a previously unfilled device for application of a composite composition.

The invention additionally relates to a method for preparing a dental treatment of a patient, having the following step:

heating a composite composition according to the invention or a device according to the invention comprising a composite composition according to the invention to a temperature of 40° C. or more, preferably a temperature in the range from 40° C. to 80° C., preferably in an oven and/or by irradiation, preferably with IR rays.

The invention also encompasses a method of treatment of a tooth, having the following steps:

producing or providing a composite composition according to the invention, heating the composite composition according to the invention to a temperature of 40° C. or more, preferably a temperature in the range from 40° C. to 80° C., preferably in an oven and/or by irradiation, preferably with IR rays, contacting the composite composition according to the invention that has been heated to a temperature of 40° C. or more, preferably a temperature in the range from 40° C. to 80° C., with a patient's tooth to be treated, preferably as dental filling material, lining material, luting material and fissure sealant.

The invention is described in detail hereinafter.

EXAMPLES

Abbreviations

TEGDMA: triethylene glycol dimethacrylate
GDMA: glycerol 1,3-dimethacrylate
DODMA: dodecane-1,12-diol dimethacrylate
TCDDMA: bis(methacryloyloxymethyl)tricyclo[$5.2.1.0^{2,6}$] decane
TCD-2EO-DMA: bis(methacryloyl-2-oxyethyloxymethyl) tricyclo[$5.2.1.0^{2,6}$]decane BCHDMA: bis(hydroxymethyl)bicyclo[2.2.1]heptane
UDMA: 7,7,9-trimethyl-4,13-dioxo-3,14-dioxa-5,12-diazahexadecane 1,16-dioxydimethacrylate
BisEMA: ethoxylated bisphenol A dimethacrylate having an average of 2.6 ethylene oxide units
BisGMA: 2,2-bis[4-(2-hydroxy-3-methacryloyloxypropyloxy)phenyl]propane)
MDI-HEMA: addition product of diisocyanatodiphenylmethane (MDI) with HEMA (hydroxyethyl methacrylate)
TMXDI-HEMA: addition product of tetramethylxylylene diisocyanate (TMXDI) with HEMA (hydroxyethyl methacrylate)
Polysiloxane 1: condensation product of 3-methacryloyloxypropyldimethoxymethylsilane (for synthesis see further up)
Dental glass 1: barium aluminium borosilicate glass (D50 0.8 µm/D25 0.5 µm/D75 1.0 µm), silanized with γ-methacryloyloxypropyltrimethoxysilane
Dental glass 2: barium aluminium borosilicate glass (D50 2.7 µm/D25 1.4 µm/D75 6.1 µm), silanized with γ-methacryloyloxypropyltrimethoxysilane
Dental glass 3: barium aluminium borosilicate glass (D50 0.8 µm/D25 0.5 µm/D75 1.0 µm), silanized with 2-(methacryloyloxy)ethyl [3-(triethoxysilyl)propyl]-carbamate
Dental glass 4: barium aluminium borosilicate glass (D50 2.7 µm/D25 1.4 µm/D75 6.1 µm), silanized with 2-(methacryloyloxy)ethyl [3-(triethoxysilyl)propyl]-carbamate
Nano-SiO$_2$ 1: non-agglomerated, non-aggregated silica (D50 40 nm), silanized with γ-methacryloyloxypropyltrimethoxysilane
Nano-SiO$_2$ 2: non-agglomerated, non-aggregated silica (D50 40 nm), silanized with 2-(methacryloyloxy)ethyl [3-(triethoxysilyl)propyl]carbamate
Fumed SiO$_2$: Aerosil R709

Preparation of the Resins:

The appropriate methacrylate monomers were homogenized at room temperature with the aid of a precision glass stirrer. The initiators and inhibitors were already dissolved directly in the resin.

Production of the Composites

For production of the composites, the monomer mixtures with the initiators and inhibitors dissolved therein were initially charged in each case, the fillers were added stepwise and the mixture was homogenized in a Hauschild mixer. Subsequently, the finished composite was degassed at room temperature under reduced pressure (−0.85 bar).

Rheometer Measurement:

The standard method of rheometer measurement was on an Anton Paar rheometer of the Physica MCR 301 type with a 12 mm measurement plate (plate/plate), gap margin 1 mm and 450 mg of substance.

The method of measuring the viscosities of the composites at 20° C. and at 50° C. comprises three successive sections. Prior to the measurement, the plate is equilibrated to a temperature of 20° C. In Phase I of the measurement, measurement is effected at 20° C. for five minutes at a deformation of 1% and an oscillation frequency of 300 rad/s. The last point at the temperature at which the viscosity of the composite reaches its final value is used for evaluation. In Phase II, measurement is likewise effected under the same deformation and oscillation conditions at a temperature of 50° C. for five minutes and, analogously to Phase I, the last point is used for evaluation. Phase III corresponds to Phase I again, in which the viscosity of the composite then gradually approaches the original value again.

Analogously, for some examples, the viscosities were determined at 37° C. and 68° C., with measurement in the three sections at temperatures of 37° C., 68° C. and 37° C. rather than 20° C., 50° C. and 20° C.

Flexural strength (FS): Flexural strengths were determined in accordance with ISO 4049:2009. The composite pastes were applied in moulds of dimensions 25 mm×2 mm×2 mm and light-cured with a Celalux 2 lamp (VOCO GmbH) in sections for 40 seconds each. Flexural strength is determined at an advance rate of 0.75 mm/min using a Zwick universal tester (Zwick GmbH & Co. KG, Ulm).

For Fixing of the Limits:

FIG. 1 shows, by way of example, the temperature dependence of viscosity for Example 1. A material having a viscosity of more than 400 Pa*s (at room temperature) is malleable. The material is still just modellable at a temperature of 37° C. (intraoral temperature). At 50° C., a viscosity below 150 Pa*s is attained and the material begins to flow. In the dental practice, the composites, according to the model and type of heating unit, are preheated to a temperature of about 70° C. The inventive composition from Example 1 reaches a viscosity of 54.8 Pa*s at 68° C. and is thus exceptionally free-flowing since a viscosity corresponding to that of the commercially available free-flowing composite GrandioSO Heavy Flow is attained here. This flow composite serves as a reference for demonstration of flowability of formerly malleable composite materials. If it is assured that the composites at 50° C. have a viscosity below 150 Pa*s, the flowability thereof on preheating corresponds exactly to that of a material developed for flowability at room temperature.

The thermal efficacy or thermal effect of a dental composite composition can be illustrated by the following relationship:

$$\text{Thermal effect} = \frac{\eta(20°\text{ C.}) - \eta(50°\text{ C.})}{\eta(20°\text{ C.})} \times 100\%$$

A quotient $\eta_{50}/\eta_{20}$ of 0.125 thus corresponds to a thermal effect of 87.5%, and a quotient $\eta_{50}/\eta_{20}$ of 0.1 corresponds to a thermal effect of 90%. Thus, the greater the difference in its viscosities at the two temperatures stipulated, the greater the thermal effect of a dental composite composition. These values reflect the property of the composite composition according to the invention of attaining a maximum viscosity at the preparation temperature and a minimum viscosity at the treatment temperature. For the dental composite composition, this means:
 1.) a clean, reliable, contamination-free approach prior to application,
 2.) application at an exact location with rapid, complete adaptation to the cavity margins,
 3.) transformation of the free-flowing phase back to malleability and hence excellent modellability for the dentist.

Thus, malleability is sufficient especially when both the viscosity $\eta_{20}$ at 20° C. and the viscosity $\eta_{37}$ at 37° C. are greater than 400 Pa*s. This is because, in that case, the composite compositions according to the invention can both be handled cleanly and without contamination at room temperature and modelled efficiently at intraoral temperature.

Table 1 contains, by way of example, the numerical values for the thermal efficacy of commercially available dental composites.

No commercially available dental composites have a sufficient thermal effect and the required values of viscosity before and after heating, and so there are no malleable products on the market to date that have a viscosity that decreases disproportionately on heating, and so adapt efficiently to the prepared cavity margins in the heated state—in a comparable manner to the flow composites—in order to switch back to the malleable state with increasing cooling, to have good modellability and then, after light curing, to have the excellent mechanical properties of highly filled dental composites.

Dental compositions with light-curable bi- or tricyclic systems are known from the prior art.

Published specification DE 28 16 823 describes curable dental compounds for dental fillings, dental prostheses and as sealing compounds that comprise di(meth)acrylates of bis(hydroxymethyl)tricyclo[5.2.1.0$^{2,6}$]decane. Example 9 describes a two-component paste/paste system composed of the diacrylate of bis(hydroxymethyl)tricyclo[5.2.1.0$^{2,6}$]decane with the propoxylated dimethacrylate of bisphenol A. Examples 12 and 13 disclose light-curable, one-component composite compositions which include, as organic matrix, diacrylates of bis(hydroxymethyl)tricyclo[5.2.1.0$^{2,6}$]decane. Example 15 discloses a light-curable coating compound based on the dimethacrylate of bis(hydroxymethyl)tricyclo[5.2.1.0$^{2,6}$]decane in combination with hexanediol dimethacrylate.

Published specification DE 29 31 926 describes the (meth)acrylates of alkoxylated bis(hydroxymethyl)tricyclo[5.2.1.0$^{2,6}$]decane as a suitable binder for curable dental compounds. These tricyclic systems are said to be suitable as diluent monomers for high-viscosity dental standard monomers such as bis-GMA (bisphenol A glycidyl methacrylate). For production of mixed binders, the (meth)acrylates of alkoxylated bis(hydroxymethyl)tricyclo[5.2.1.0$^{2,6}$]decane can be used together with ethylene glycol di(meth)acrylate, triethylene glycol di(meth)acrylate, trimethylolpropane tri(meth)acrylate, pentaerythritol tetraacrylate, butane-1,3-diol di(meth)acrylate and hexane-1,6-diol di(meth)acrylate.

Example 14 discloses a two-component chemical curable dental composite composition, the resin matrix of which consists of 70 parts bis(hydroxymethyl)tricyclo[5.2.1.0$^{2,6}$]decane and 30 parts bis-GMA. Example 19 reports a one-component, radiation-curable composite composition including, as resin matrix, the propoxylated dimethacrylate of bis(hydroxymethyl)tricyclo[5.2.1.0$^{2,6}$]decane.

Published specification DE 29 31 925—like the above-cited DE 29 31 926—relates to (meth)acrylates of tricyclic decanediols containing ether groups. The alkoxylated tricyclic systems are suitable for use for production of adhesives and sealants and for production of dental repair materials.

U.S. Pat. No. 4,131,729 also specifies dental, light-curable composite compositions of the (meth)acrylates of bis(hydroxymethyl)tricyclo[5.2.1.0$^{2,6}$]decane (Examples 12, 13 and 15). The tricyclic system can be used alone or in combination with other monomers. The text says "Known bifunctional monomers which are particularly suitable for novel combinations with the monomers of the invention are the di(meth)acrylates of hexanediol, bis(p-hydroxyethoxy)phenylpropane, or bis-[p-(gamma-hydroxypropoxy)phenyl]propane."

DE 2 200 021, entitled "Acrylic esters of tricyclic decanols containing OH groups", claims tricyclodecane derivatives for use in curable adhesives for production of heat-resistant bonds.

Further (meth)acrylates of tricyclic decanols are described in documents DE 24 06 557, DE 35 22 005, DE 35 22 006 and DE 37 03 120.

DE 10 2005 021 332 A1 claims dental composite materials having low shrinkage. The resin matrix of the curable composition comprises bis-GMA or the tricyclic derivative TCD-di-HEMA or the tricyclic derivative TCD-di-HEA in an amount of 60-80% by weight, 10% to 18% by weight of UDMA (urethane dimethacrylate) and the balance TEDMA and/or multifunctional crosslinkers, where the percentages by weight are based on the resin phase.

DE 10 2007 034 457 A1 claims dental composite materials having low shrinkage stress and high flexural strength. The resin matrix of the curable composition contains bis-GMA and a member from the group of TCD-di-HEMA and TCD-di-HEA in an amount of 60-80% by weight, 10-18% by weight of UDMA and as the balance TEDMA and/or multifunctional crosslinkers, where the percentages by weight are based on the resin phase.

EP 2 436 366 B1 is directed to a composite material which comprises a monomer having a polyalicyclic structural element and is used as sealing material. In Examples 3 and 4 (Table 1), bis(methacryloyloxymethyl)tricyclo[5.2.1.0$^{2,6}$]decane is used together with bis-GMA. However, the total filler content is well below 70% by weight based on the composite composition and the proportion of the tricyclodecane derivative far exceeds the proportion of bis-GMA.

TABLE 1

| Commercial composite | $\eta(20°\,C.)$ [Pa·s] | $\eta(50°\,C.)$ [Pa·s] | $\dfrac{\eta(50°\,C.)}{\eta(20°\,C.)}$ | $\dfrac{\eta(20°\,C.) - \eta(50°\,C.)}{\eta(20°\,C.)} \times 100\%$ |
|---|---|---|---|---|
| Filtek Supreme XTE (3M Espe) | 2045 | 869 | 0.42 | 57.5% |
| Clearfil Majesty Posterior (Kuraray) | 3147 | 2135 | 0.68 | 32.2% |
| Ceram X (Dentsply) | 1422 | 368 | 0.26 | 74.1% |
| Sonic Fill (Kerr) | 419 | 257 | 0.61 | 38.7% |
| Sonic Fill 2 (Kerr) | 1019 | 683 | 0.67 | 33.0% |
| Ecosite Universal Bulk Fill (DMG) | 460 | 221 | 0.48 | 51.9% |
| Esthet-X (Dentsply) | 923 | 250 | 0.27 | 73.2% |
| GrandioSO Heavy Flow (VOCO) | 53.3 | n.d. | n.d. | n.d. |

TABLE 2

| Example | | | 1 | 2 | 3 |
|---|---|---|---|---|---|
| (A) Monomers | (A1) | TCDDMA | 4.23 | 4.63 | 6.04 |
| | (A2) | BisGMA | 16.90 | 10.87 | 9.11 |
| | (A3) | UDMA | | | |
| (B) Fillers | (B1) | Nano-SiO$_2$ 1 | 6.28 | 14.76 | 14.56 |
| | (B2) | Dental glass 2 | 60.33 | 58.02 | 58.49 |
| | (B3) | Dental glass 1 | 12.04 | 11.59 | 11.68 |
| (C) Initiators | (C1) | CQ | 0.06 | 0.04 | 0.04 |
| | (C2) | DABE | 0.10 | 0.07 | 0.07 |
| (D) Others | (D1) | BHT | 0.06 | 0.02 | 0.01 |
| | | Total | 100.00 | 100.00 | 100.00 |
| Viscosity η(20° C.) [Pa · s] | | | 2290.2 | 1974.1 | 1405.9 |
| Viscosity η(37° C.) [Pa · s] | | | 505.8 | 473.3 | 449.7 |
| Viscosity η(50° C.) [Pa · s] | | | 142.3 | 134.1 | 136.7 |
| Viscosity η(68° C.) [Pa · s] | | | 54.8 | 54.1 | 53.5 |
| $\frac{\eta(50° C.)}{\eta(20° C.)}$ | | | 0.06 | 0.07 | 0.10 |
| Thermal effect $\frac{\eta(20° C.) - \eta(50° C.)}{\eta(20° C.)} \times 100\%$ | | | 93.8% | 93.2% | 90.3% |
| Flexural strength [MPa] | | | 155.4 | 149.6 | 154.8 |

TABLE 3

| Example | | | 4 | 5 | 6 |
|---|---|---|---|---|---|
| (A) Monomers | (A1) | TCDDMA | 6.34 | 5.21 | 4.56 |
| | (A2) | BisGMA | 14.79 | 12.17 | 10.71 |
| | (A3) | UDMA | | | |
| (B) Fillers | (B1) | Nano-SiO$_2$ 1 | 6.28 | 9.26 | 16.67 |
| | (B2) | Dental glass 2 | 60.33 | 61.02 | 58.24 |
| | (B3) | Dental glass 1 | 12.04 | 12.19 | 9.69 |
| (C) Initiators | (C1) | CQ | 0.06 | 0.05 | 0.05 |
| | (C2) | DABE | 0.10 | 0.08 | 0.07 |
| (D) Others | (D1) | BHT | 0.06 | 0.02 | 0.01 |
| | | Total | 100.00 | 100.00 | 100.00 |
| Viscosity η(20° C.) [Pa · s] | | | 1502.3 | 1253.4 | 1817.7 |
| Viscosity η(50° C.) [Pa · s] | | | 123.9 | 134.5 | 142.3 |
| $\frac{\eta(50° C.)}{\eta(20° C.)}$ | | | 0.08 | 0.11 | 0.08 |
| Thermal effect $\frac{\eta(20° C.) - \eta(50° C.)}{\eta(20° C.)} \times 100\%$ | | | 91.8% | 89.3% | 92.2% |
| Flexural strength [MPa] | | | 141.0 | 134.9 | 152.4 |

TABLE 4

| Example | | | 7 | 8 | 9 |
|---|---|---|---|---|---|
| (A) Monomers | (A1) | TCDDMA | 7.38 | 5.74 | 8.55 |
| | (A2) | BisGMA | 17.23 | 13.39 | 8.11 |
| | (A3) | UDMA | | | 2.00 |
| (B) Fillers | (B1) | Nano-SiO$_2$ 1 | 3.00 | 6.28 | 14.16 |
| | (B2) | Dental glass 2 | 60.17 | 60.33 | 57.55 |
| | (B3) | Dental glass 1 | 12.01 | 12.04 | 11.51 |
| (C) Initiators | (C1) | CQ | 0.07 | 0.06 | 0.04 |
| | (C2) | DABE | 0.11 | 0.10 | 0.07 |
| (D) Others | (D1) | BHT | 0.03 | 0.06 | 0.02 |
| | | Total | 100.00 | 100.00 | 100.00 |
| Viscosity η(20° C.) [Pa · s] | | | 1387.2 | 1465.2 | 1203.1 |
| Viscosity η(50° C.) [Pa · s] | | | 112.8 | 118.1 | 145.4 |
| $\frac{\eta(50° C.)}{\eta(20° C.)}$ | | | 0.08 | 0.08 | 0.12 |

TABLE 4-continued

| Example | | 7 | 8 | 9 |
|---|---|---|---|---|
| Thermal effect $\frac{\eta(20° C.) - \eta(50° C.)}{\eta(20° C.)} \times 100\%$ | | 91.9% | 91.9% | 87.9% |
| Flexural strength [MPa] | | 128.2 | 135.0 | 123.7 |

TABLE 5

| Example | | | 10 | 11 | 12 |
|---|---|---|---|---|---|
| (A) Monomers | (A1) | TCDDMA | 7.51 | | |
| | | TCD-2EO-DMA | | 4.63 | |
| | | BDHDMA | | | 4.63 |
| | (A2) | BisGMA | 17.43 | 10.87 | 10.87 |
| | (A3) | UDMA | | | |
| (B) Fillers | (B1) | Fumed SiO$_2$ | 2.20 | | |
| | | Nano-SiO$_2$ 1 | | 14.76 | 14.76 |
| | (B2) | Dental glass 2 | 60.57 | 58.02 | 58.02 |
| | (B3) | Dental glass 1 | 12.11 | 11.59 | 11.59 |
| (C) Initiators | (C1) | CQ | 0.06 | 0.04 | 0.04 |
| | (C2) | DABE | 0.10 | 0.07 | 0.07 |
| (D) Others | (D1) | BHT | 0.02 | 0.02 | 0.02 |
| | | Total | 100.00 | 100.00 | 100.00 |
| Viscosity η(20° C.) [Pa · s] | | | 1488.6 | 1966.3 | 1908.4 |
| Viscosity η(50° C.) [Pa · s] | | | 143.6 | 139.8 | 142.1 |
| $\frac{\eta(50° C.)}{\eta(20° C.)}$ | | | 0.10 | 0.07 | 0.07 |
| Thermal effect $\frac{\eta(20° C.) - \eta(50° C.)}{\eta(20° C.)} \times 100\%$ | | | 90.4% | 92.9% | 92.6% |
| Flexural strength [MPa] | | | 127.0 | 142.1 | 135.6 |

TABLE 6

| Example | | | 13 | 14 | 15 |
|---|---|---|---|---|---|
| (A) Monomers | (A1) | TCDDMA | 4.63 | 6.20 | 5.03 |
| | (A2) | BisGMA | 10.87 | | |
| | | MDI-HEMA | | 9.30 | |
| | | TMXDI-HEMA | | | 10.47 |
| | (A3) | UDMA | | | |
| (B) Fillers | (B1) | Nano-SiO$_2$ 1 | | 14.76 | 14.76 |
| | | Nano-SiO$_2$ 2 | 14.76 | | |
| | (B2) | Dental glass 2 | | 58.02 | 58.02 |
| | | Dental glass 4 | 58.02 | | |
| | (B3) | Dental glass 1 | | 11.59 | 11.59 |
| | | Dental glass 3 | 11.59 | | |
| (C) Initiators | (C1) | CQ | 0.04 | 0.04 | 0.04 |
| | (C2) | DABE | 0.07 | 0.07 | 0.07 |
| (D) Others | (D1) | BHT | 0.02 | 0.02 | 0.02 |
| | | Total | 100.00 | 100.00 | 100.00 |
| Viscosity η(20° C.) [Pa · s] | | | 2344.5 | 1641.1 | 1588.7 |
| Viscosity η(50° C.) [Pa · s] | | | 117.3 | 148.7 | 147.3 |
| $\frac{\eta(50° C.)}{\eta(20° C.)}$ | | | 0.05 | 0.09 | 0.09 |
| Thermal effect $\frac{\eta(20° C.) - \eta(50° C.)}{\eta(20° C.)} \times 100\%$ | | | 95.0% | 90.9% | 90.7% |
| Flexural strength [MPa] | | | 153.1 | 128.4 | 123.5 |

TABLE 7

| Example | | | 16 |
|---|---|---|---|
| (A) Monomers | (A1) | TCDDMA | 7.21 |
| | (A2) | BisGMA | 16.81 |
| | (A3) | UDMA | |
| (B) Fillers | (B1) | Nano-SiO$_2$ 1 | 6.28 |
| | (B2) | Dental glass 2 | 57.92 |
| | (B3) | Dental glass 1 | 11.56 |
| (C) Initiators | (C1) | CQ | 0.06 |
| | (C2) | DABE | 0.10 |
| (D) Others | (D1) | BHT | 0.06 |
| | | Total | 100.00 |
| Viscosity η(20° C.) [Pa · s] | | | 502.2 |
| Viscosity η(50° C.) [Pa · s] | | | 62.5 |
| $\dfrac{\eta(50°\ C.)}{\eta(20°\ C.)}$ | | | 0.124 |
| Thermal effect $\dfrac{\eta(20°\ C.) - \eta(50°\ C.)}{\eta(20°\ C.)} \times 100\%$ | | | 87.6% |
| Flexural strength [MPa] | | | 127.2 |

TABLE 8

| Example | | | 17 | 18 | 19 |
|---|---|---|---|---|---|
| (A) Monomers | (A4) | UDMA | 3.84 | 4.48 | 5.17 |
| | (A2) | BisGMA | 11.01 | 11.28 | 11.64 |
| | (A5) | TEGDMA | 2.62 | 2.15 | 1.66 |
| (B) Fillers | (B1) | Nano-SiO$_2$ 1 | 10.00 | 10.00 | 10.00 |
| | (B2) | Dental glass 2 | 60.33 | 59.97 | 59.50 |
| | (B3) | Dental glass 1 | 12.07 | 11.99 | 11.90 |
| (C) Initiators | (C1) | CQ | 0.04 | 0.04 | 0.04 |
| | (C2) | DABE | 0.07 | 0.07 | 0.07 |
| (D) Others | (D1) | BHT | 0.02 | 0.02 | 0.02 |
| | | Total | 100.00 | 100.00 | 100.00 |
| Viscosity η(20° C.) [Pa · s] | | | 708 | 1069 | 1211 |
| Viscosity η(37° C.) [Pa · s] | | | 322 | 402 | 431 |
| Viscosity η(50° C.) [Pa · s] | | | 128 | 133 | 145 |
| Viscosity η(68° C.) [Pa · s] | | | 51 | 52 | 54 |
| $\dfrac{\eta(50°\ C.)}{\eta(20°\ C.)}$ | | | 0.181 | 0.124 | 0.120 |
| Thermal effect $\dfrac{\eta(20°\ C.) - \eta(50°\ C.)}{\eta(20°\ C.)} \times 100\%$ | | | 81.9% | 87.6% | 88.0% |
| Flexural strength [MPa] | | | 136.4 | 137.2 | 137.9 |

TABLE 9

| Example | | | 20 | 21 | 22 |
|---|---|---|---|---|---|
| (A) Monomers | (A4) | BisEMA | 5.83 | 5.22 | 4.66 |
| | (A2) | BisGMA | 10.82 | 12.18 | 13.99 |
| | (A5) | TEGDMA | | | |
| (B) Fillers | (B1) | Nano-SiO$_2$ 1 | 9.00 | 9.00 | 9.00 |
| | (B2) | Dental glass 2 | 61.85 | 61.22 | 60.18 |
| | (B3) | Dental glass 1 | 12.37 | 12.24 | 12.04 |
| (C) Initiators | (C1) | CQ | 0.04 | 0.04 | 0.04 |
| | (C2) | DABE | 0.07 | 0.07 | 0.07 |
| (D) Others | (D1) | BHT | 0.02 | 0.02 | 0.02 |
| | | Total | 100.00 | 100.00 | 100.00 |
| Viscosity η(20° C.) [Pa · s] | | | 1045 | 1233 | 1568 |
| Viscosity η(50° C.) [Pa · s] | | | 125 | 137 | 147 |
| $\dfrac{\eta(50°\ C.)}{\eta(20°\ C.)}$ | | | 0.120 | 0.111 | 0.094 |
| Thermal effect $\dfrac{\eta(20°\ C.) - \eta(50°\ C.)}{\eta(20°\ C.)} \times 100\%$ | | | 88.0% | 88.9% | 90.6% |
| Flexural strength [MPa] | | | 135.3 | 142.1 | 139.9 |

TABLE 10

| Example | | | 23 | 24 | 25 |
|---|---|---|---|---|---|
| (A) Monomers | (A4) | DIPENTA | 4.19 | 4.83 | 5.54 |
| | (A2) | BisGMA | 11.01 | 11.28 | 11.64 |
| | (A5) | TEGDMA | 2.27 | 1.79 | 1.29 |
| (B) Fillers | (B1) | Nano-SiO$_2$ 1 | 10.00 | 10.00 | 10.00 |
| | (B2) | Dental glass 2 | 60.33 | 59.97 | 59.50 |
| | (B3) | Dental glass 1 | 12.07 | 11.99 | 11.90 |
| (C) Initiators | (C1) | CQ | 0.04 | 0.04 | 0.04 |
| | (C2) | DABE | 0.07 | 0.07 | 0.07 |
| (D) Others | (D1) | BHT | 0.02 | 0.02 | 0.02 |
| | | Total | 100.00 | 100.00 | 100.00 |
| Viscosity η(20° C.) [Pa · s] | | | 941 | 1156 | 1311 |
| Viscosity η(50° C.) [Pa · s] | | | 131 | 139 | 147 |
| $\dfrac{\eta(50°\ C.)}{\eta(20°\ C.)}$ | | | 0.139 | 0.120 | 0.112 |
| Thermal effect $\dfrac{\eta(20°\ C.) - \eta(50°\ C.)}{\eta(20°\ C.)} \times 100\%$ | | | 86.1% | 88.0% | 88.8% |
| Flexural strength [MPa] | | | 121.4 | 125.3 | 122.1 |

TABLE 11

| Example | | | 26 | 27 | 28 |
|---|---|---|---|---|---|
| (A) Monomers | (A4) | TCDDMA | 3.13 | 2.28 | 1.59 |
| | | UDMA | 3.88 | 3.73 | 3.58 |
| | (A2) | BisGMA | 13.58 | 13.88 | 13.91 |
| | (A5) | TEGDMA | 0.97 | 0.83 | 0.79 |
| (B) Fillers | (B1) | Nano-SiO$_2$ 1 | 4.72 | 4.36 | 4.00 |
| | (B2) | Dental glass 2 | 61.33 | 54.67 | 48.00 |
| | (B3) | Dental glass 1 | 12.27 | 20.13 | 28.00 |
| (C) Initiators | (C1) | CQ | 0.04 | 0.04 | 0.04 |
| | (C2) | DABE | 0.07 | 0.07 | 0.07 |
| (D) Others | (D1) | BHT | 0.02 | 0.02 | 0.02 |
| | | Total | 100.00 | 100.00 | 100.00 |
| Viscosity η(20° C.) [Pa · s] | | | 1570 | 1588 | 1592 |
| Viscosity η(50° C.) [Pa · s] | | | 149 | 128 | 102 |
| $\dfrac{\eta(50°\ C.)}{\eta(20°\ C.)}$ | | | 0.095 | 0.081 | 0.064 |
| Thermal effect $\dfrac{\eta(20°\ C.) - \eta(50°\ C.)}{\eta(20°\ C.)} \times 100\%$ | | | 90.5% | 91.9% | 93.6% |
| Flexural strength [MPa] | | | 141.1 | 137.7 | 140.5 |

TABLE 12

| Example | | | 29 | 30 | 31 |
|---|---|---|---|---|---|
| (A) Monomers | (A4) | UDMA | 5.17 | 5.17 | 5.27 |
| | (A2) | BisGMA | 5.82 | | 5.75 |
| | | MDI-HEMA | 5.82 | 11.64 | |
| | | TMXDI-HEMA | | | 5.75 |
| | (A5) | TEGDMA | 1.66 | 1.66 | 1.70 |

TABLE 12-continued

| Example | | | 29 | 30 | 31 |
|---|---|---|---|---|---|
| (B) Fillers | (B1) | Nano-SiO$_2$ 1 | 10.00 | 10.00 | 10.00 |
| | (B2) | Dental glass 2 | 59.50 | 59.50 | 59.50 |
| | (B3) | Dental glass 1 | 11.90 | 11.90 | 11.90 |
| (C) Initiators | (C1) | CQ | 0.04 | 0.04 | 0.04 |
| | (C2) | DABE | 0.07 | 0.07 | 0.07 |
| (D) Others | (D1) | BHT | 0.02 | 0.02 | 0.02 |
| | | Total | 100.00 | 100.00 | 100.00 |
| Viscosity η(20° C.) [Pa · s] | | | 1723 | 1952 | 1984 |
| Viscosity η(50° C.) [Pa · s] | | | 147 | 150 | 143 |
| $\frac{\eta(50°\ C.)}{\eta(20°\ C.)}$ | | | 0.085 | 0.077 | 0.072 |
| Thermal effect $\frac{\eta(20°\ C.) - \eta(50°\ C.)}{\eta(20°\ C.)} \times 100\%$ | | | 91.5% | 92.3% | 92.8% |
| Flexural strength [MPa] | | | 129 | 133 | 138 |

TABLE 13

| Example | | | 32 | 33 | 34 |
|---|---|---|---|---|---|
| (A) Monomers | (A4) | Polysiloxane 1 | 6.17 | 9.57 | 18.12 |
| | (A2) | BisGMA | 11.64 | 9.57 | |
| | (A5) | TEGDMA | 0.66 | | |
| (B) Fillers | (B1) | Nano-SiO$_2$ 1 | 9.00 | 8.99 | 8.99 |
| | (B2) | Dental glass 2 | 60.33 | 59.78 | 60.63 |
| | (B3) | Dental glass 1 | 12.07 | 11.96 | 12.13 |
| (C) Initiators | (C1) | CQ | 0.04 | 0.04 | 0.04 |
| | (C2) | DABE | 0.07 | 0.07 | 0.07 |
| (D) Others | (D1) | BHT | 0.02 | 0.02 | 0.02 |
| | | Total | 100.00 | 100.00 | 100.00 |
| Viscosity η(20° C.) [Pa · s] | | | 1665 | 2029 | 1789 |
| Viscosity η(50° C.) [Pa · s] | | | 149 | 147 | 143 |
| $\frac{\eta(50°\ C.)}{\eta(20°\ C.)}$ | | | 0.089 | 0.072 | 0.080 |
| Thermal effect $\frac{\eta(20°\ C.) - \eta(50°\ C.)}{\eta(20°\ C.)} \times 100\%$ | | | 91.1% | 92.8% | 92.0% |
| Flexural strength [MPa] | | | 132.2 | 131.0 | 134.7 |

TABLE 14

| Comparative Example | | | V1 | V2 | V3 |
|---|---|---|---|---|---|
| (A) Monomers | (A1) | TCDDMA | 12.47 | | 5.92 |
| | (A2) | BisGMA | 5.34 | | |
| | (A3) | UDMA | | 13.67 | 8.89 |
| | | BisEMA | | | |
| (B) Fillers | (B1) | Nano-SiO$_2$ 1 | 13.55 | 17.68 | 13.05 |
| | (B2) | Dental glass 2 | 57.10 | 57.12 | 60.03 |
| | (B3) | Dental glass 1 | 11.41 | 11.39 | 11.94 |
| (C) Initiators | (C1) | CQ | 0.04 | 0.04 | 0.05 |
| | (C2) | DABE | 0.07 | 0.06 | 0.07 |
| (D) Others | (D1) | BHT | 0.02 | 0.04 | 0.05 |
| | | Total | 100.00 | 100.00 | 100.00 |
| Viscosity η(20° C.) [Pa · s] | | | 233.9 | 1522.3 | 678.8 |
| Viscosity η(50° C.) [Pa · s] | | | 105.8 | 550.5 | 310.1 |
| $\frac{\eta(50°\ C.)}{\eta(20°\ C.)}$ | | | 0.45 | 0.36 | 0.46 |
| Thermal effect $\frac{\eta(20°\ C.) - \eta(50°\ C.)}{\eta(20°\ C.)} \times 100\%$ | | | 54.8% | 63.8% | 54.3% |
| Flexural strength [MPa] | | | 118.8 | 162.9 | 156.7 |

TABLE 15

| Comparative Example | | | V4 | V5 | V6 |
|---|---|---|---|---|---|
| (A) Monomers | (A1) | TCDDMA | 7.74 | 3.98 | 9.96 |
| | (A2) | BisGMA | | | |
| | (A3) | UDMA | 11.61 | | |
| | | BisEMA | | 10.47 | 4.49 |
| (B) Fillers | (B1) | Nano-SiO$_2$ 1 | 5.75 | 13.14 | 13.14 |
| | (B2) | Dental glass 2 | 62.25 | 60.30 | 60.30 |
| | (B3) | Dental glass 1 | 12.44 | 12.04 | 12.04 |
| (C) Initiators | (C1) | CQ | 0.06 | 0.02 | 0.02 |
| | (C2) | DABE | 0.09 | 0.03 | 0.03 |
| (D) Others | (D1) | BHT | 0.06 | 0.02 | 0.02 |
| | | Total | 100.00 | 100.00 | 100.00 |
| Viscosity η(20° C.) [Pa · s] | | | 206.7 | 377.0 | 314.8 |
| Viscosity η(50° C.) [Pa · s] | | | 95.6 | 242.8 | 189.1 |
| $\frac{\eta(50°\ C.)}{\eta(20°\ C.)}$ | | | 0.46 | 0.64 | 0.60 |
| Thermal effect $\frac{\eta(20°\ C.) - \eta(50°\ C.)}{\eta(20°\ C.)} \times 100\%$ | | | 53.7% | 35.6% | 39.9% |
| Flexural strength [MPa] | | | 159.8 | 139.4 | 130.0 |

Relevant aspects of the present invention are summarized hereinafter:

Aspects:

1. Dental, light-curable, one-component composite composition, comprising:
   (A) monomers,
   (B) fillers, and
   (C) initiators,
   characterized in that
      the viscosity $\eta_{20}$ of the composite composition at 20° C. is greater than 400 Pa*s and
      the viscosity $\eta_{50}$ of the composite composition at 50° C. is less than 150 Pa*s and
      the quotient $\eta_{50}/\eta_{20}$ of the viscosity of the composite composition at 50° C. and the viscosity of the composite composition at 20° C. is less than 0.125.

2. Dental, light-curable, one-component composite composition according to Aspect 1, wherein
   the viscosity $\eta_{20}$ of the composite composition at 20° C. is greater than 800 Pa*s, preferably greater than 1200 Pa*s, and/or
   the viscosity $\eta_{50}$ of the composite composition at 50° C. is less than 120 Pa*s, preferably less than 90 Pa*s, and/or
   the quotient $\eta_{50}/\eta_{20}$ of the viscosity of the composite composition at 50° C. and the viscosity of the composite composition at 20° C. is less than 0.1.

3. Dental, light-curable, one-component composite composition according to any of the preceding aspects, wherein the viscosity $\eta_{37}$ of the composite composition at 37° C. is greater than 400 Pa*s.

4. Dental, light-curable, one-component composite composition according to any of the preceding aspects, selected from the group consisting of dental filling material, lining material, luting material and fissure sealant.

5. Dental, light-curable, one-component composite composition according to any of the preceding aspects, comprising:
   (A) monomers in an amount of 6% to 35% by weight, based on the total amount of the composite composition, preferably 10% to 35% by weight, more preferably 10% to 25% by weight,
   (B) fillers in an amount of 65% to 93% by weight, based on the total amount of the composite composition, preferably 65% to 89% by weight, more preferably 75% to 89% by weight, (C) initiators in an amount of 0.001% to 3% by weight, based on the total amount of the composite composition, (D) further additives in an amount of 0.001% to 5% by weight, based on the total amount of the composite composition.

6. Dental, light-curable, one-component composite composition according to any of the preceding aspects, wherein constituent (A) comprises a mixture of at least
   (A-i) one first monomer substance and
   (A-ii) one second monomer substance,
   wherein
   the viscosity $\eta_{20}$ of the second monomer substance (A-ii) at 20° C. is greater than 100 Pa*s,
   the viscosity $\eta_{20}$ of the first monomer substance (A-i) at 20° C. is greater than 100 mPa*s,
   the viscosity of the second monomer substance (A-ii) at 20° C. is greater than that of the first monomer substance (A-i) and
   the mass ratio of the first monomer substance (A-i) to the second monomer substance (A-ii) is in the range from 2:1 to 1:10,
   wherein the second monomer substance (A-ii) preferably contains at least 40% by weight of 2,2-bis[4-(2-hydroxy-3-methacryloyloxypropoxy)phenyl]propane (bis-GMA) and/or light-curable derivatives of diisocyanatodiphenylmethane (MDI) and/or light-curable derivatives of tetramethyl-m-xylylene diisocyanate (TMXDI), where the percentage by weight is based on the total mass of the monomers (A).

7. Dental, light-curable, one-component composite composition, preferably according to any of the preceding aspects, wherein
   the monomers (A) consist of
   (A1) 10% to 60% by weight, preferably 20% to 50% by weight, more preferably 25% to 40% by weight, of light-curable bi- or tricyclic compounds $Q(Y_xZ_e)_b$ wherein
   Q denotes a saturated or olefinically unsaturated bi- or tricyclic structural element,
   each index b is a natural number selected from the group of the natural numbers 1, 2, and 3,
   each Z denotes a light-curable group,
   each index e is a natural number selected from the group of the natural numbers 1, 2 and 3,
   each Y in the structure $Q(Y_xZ_e)_b$ with x=1 denotes a structural element which connects the structural element Q to e structural elements Z and which denotes a straight or branched alkylene group, wherein the alkylene group may be interrupted by oxygen atoms, and each index x is 0 or 1,
   (A2) 40% to 90% by weight, preferably 50% to 80% by weight, more preferably 60% to 75% by weight, of 2,2-bis[4-(2-hydroxy-3-methacryloyloxypropoxy)phenyl]propane (bis-GMA) and/or light-curable derivatives of diisocyanatodiphenylmethane (MDI) and/or light-curable derivatives of tetramethyl-m-xylylene diisocyanate (TMXDI),
   (A3) 0% to 15% by weight, preferably 0% to 10% by weight, more preferably 0% to 5% by weight, most preferably 0% by weight, of further free-radically polymerizable monomers that cannot be assigned to (A1) or (A2),
   wherein the percentages by weight (A1), (A2) and (A3) are based on the total mass of the monomers (A).

8. Dental, light-curable, one-component composite composition according to Aspect 7, wherein Q is selected from the group of structural elements consisting of
   bicyclo[1.1.1]pentane, bicyclo[2.1.1]hexane, bicyclo[2.2.1]heptane, bicyclo[2.2.1]heptene, bicyclo[3.1.1] heptane, bicyclo[2.2.2]octane, bicyclo[4.1.1]octane, bicyclo[3.2.1]octane, bicyclo[4.2.1]nonane, bicyclo[3.3.1]nonane, bicyclo[5.1.1]nonane, bicyclo[3.2.2]nonane, bicyclo[6.1.1]decane, bicyclo[5.2.1]decane, bicyclo[4.2.2]decane, bicyclo[3.3.2]decane, bicyclo[7.1.1]undecane, bicyclo[6.2.1]undecane, bicyclo[5.2.2]undecane, bicyclo[4.3.2]undecane, bicyclo[3.3.3]undecane, bicyclo[8.1.1]dodecane, bicyclo[7.2.1]dodecane, bicyclo[6.2.2]dodecane, bicyclo[5.3.2]dodecane, bicyclo[4.3.3]dodecane, bicyclo[4.4.2]dodecane, bicyclo[5.4.1]dodecane, bicyclic tridecanes, bicyclic tetradecanes, bicyclic pentadecanes,
   tricyclo[3.2.1.0$^{2,6}$]octane, tricyclo[4.2.1.0$^{2,6}$]nonane, tricyclo[5.2.1.0$^{2,6}$]decane, tricyclo[6.2.1.0$^{2,6}$]undecane, tricyclo[7.2.1.0$^{2,6}$]dodecane, tricyclo[4.2.1.1$^{2,5}$]decane, tricyclo[4.3.1.1$^{2,5}$]decane, tricyclo[4.4.1.1$^{2,5}$]decane, tricyclo[2.2.1.0$^{2,6}$]heptane, tricyclo[2.2.2.0$^{2,6}$]octane, tricyclo[3.2.2.0$^{2,6}$]nonane, tricyclo[3.3.1.1$^{3,7}$]decane, tricyclo[3.2.1.1$^{3,7}$]nonane, tricyclo[4.2.2.2$^{2,5}$]dodecane, tricyclo[4.3.2.2$^{2,5}$]tridecane, tricyclo[4.4.2.2$^{2,5}$]tetradecane, tricyclo[4.2.1.0$^{3,7}$]nonane, tricyclo[4.4.1.1$^{1,5}$]dodecane, tricyclo[6.2.1.0$^{2,7}$]undecane, tricyclo[5.2.2.0$^{2,6}$]undecane, tricyclo[6.2.2.0$^{2,7}$]dodecane, tricyclo[4.3.2.0$^{2,5}$]undecane, tricyclo[4.2.2.0$^{2,5}$]decane and tricyclo[5.5.1.0$^{3,11}$]tridecane,
   wherein
   Q is preferably selected from the group of structural elements consisting of bicyclo[2.2.1]heptane, bicyclo[2.2.1]hept-2-ene, tricyclo[3.3.1.1$^{3,7}$]decane and tricyclo[5.2.1.0$^{2,6}$]decane and wherein Q is more preferably tricyclo[5.2.1.0$^{2,6}$]decane.

9. Dental, light-curable, one-component composite composition according to any of Aspects 7 and 8, wherein the light-curable group Z denotes a structural element selected from the group consisting of —O—(C═O)—CH═CH$_2$, —O—(C═O)—C(CH$_3$)═CH$_2$, —(C═O)—CH═CH$_2$, —(C═O)—C(CH$_3$)═CH$_2$, —CH═CH$_2$, —C(CH$_3$)═CH$_2$, —CH$_2$—CH═CH$_2$, —CH$_2$—C(CH$_3$)═CH$_2$ and —O—CH═CH$_2$, preferably selected from the group consisting of —O—(C═O)—CH═CH$_2$ and —O—(C═O)—C(CH$_3$)═CH$_2$.

10. Dental, light-curable, one-component composite composition according to any of Aspects 7 to 9, wherein
    component (A1) comprises or consists of bis(methacryloyloxymethyl)tricyclo[5.2.1.0$^{2,6}$]decane and/or alkoxylated bis(methacryloyloxymethyl)tricyclo[5.2.1.0$^{2,6}$]decane, preferably comprises or consists of bis(methacryloyloxymethyl)tricyclo[5.2.1.0$^{2,6}$]decane, and/or
    component (A2) comprises or consists of bis-GMA.

11. Dental, light-curable, one-component composite composition according to any of Aspects 7 to 10, wherein (A3) comprises one or more di(meth)acrylate monomers selected from the group consisting of ethylene glycol di(meth)acrylate, alkoxylated ethylene glycol di(meth)acrylate, diethylene glycol di(meth)acrylate, hexane-1,6-diol di(meth)acrylate, triethylene glycol di(meth)acrylate, dodecane-1,12-diol di(meth)acrylate, decane-1,10-diol di(meth)acrylate, bisphenol A di(meth)acrylate, alkoxylated bisphenol A di(meth) acrylate, polyethylene glycol di(meth)acrylate, propylene glycol di(meth)acrylate, dipropylene glycol di-(meth)acrylate, tripropylene glycol di(meth)acrylate, tetrapropylene glycol di(meth)acrylate, polypropylene glycol di(meth)acrylate, 7,7,9-trimethyl-3,14-dioxa-4,13-dioxo-5,12-diazahexadecane 1,16-dioxydi(meth)acrylate, butanediol di(meth)acrylate, propanediol di(meth)acrylate, tetraethylene glycol di(meth)acrylate, neopentyl glycol di(meth)acrylate, alkoxylated neopentyl glycol di(meth)acrylate, 2-hydroxypropyl 1,3-di(meth)acrylate, 3-hydroxypropyl 1,2-di(meth)acrylate, pentaerythritol di(meth)acrylate, alkoxylated pentaerythritol di(meth)acrylate, pentaerythritol tri(meth)acrylate, alkoxylated pentaerythritol tri(meth)acrylate, pentaerythritol tetra(meth)acrylate, alkoxylated pentaerythritol tetra(meth)acrylate, dipentaerythritol di(meth)acrylate, alkoxylated dipentaerythritol di(meth)acrylate, dipentaerythritol tri(meth)acrylate, alkoxylated dipentaerythritol tri(meth)acrylate, dipentaerythritol tetra(meth)acrylate, alkoxylated dipentaerythritol tetra(meth)acrylate, dipentaerythritol penta(meth)acrylate, alkoxylated dipentaerythritol penta(meth)acrylate, dipentaerythritol hexa(meth)acrylate, alkoxylated dipentaerythritol hexa(meth)acrylate, trimethylolpropane tri(meth)acrylate, alkoxylated trimethylolpropane tri(meth)acrylate and cyclohexanedimethanol di(meth)acrylate.

12. Dental, light-curable, one-component composite composition according to any of Aspects 1-6, wherein the monomers (A) consist of
   (A4) 10% to 60% by weight, preferably 20% to 50% by weight, more preferably 25% to 40% by weight, of one or more compounds selected from the group consisting of
      light-curable bi- or tricyclic compounds $Q(Y_xZ_e)_b$ wherein
      Q denotes a saturated or olefinically unsaturated bi- or tricyclic structural element, each index b is a natural number selected from the group of the natural numbers 1, 2, and 3,
      each Z denotes a light-curable group,
      each index e is a natural number selected from the group of the natural numbers 1, 2 and 3,
      each Y in the structure $Q(Y_xZ_e)_b$ with x=1 denotes a structural element which connects the structural element Q to e structural elements Z and which denotes a straight or branched alkylene group, wherein the alkylene group may be interrupted by oxygen atoms, and
      each index x is 0 or 1,
         7,7,9-trimethyl-3,14-dioxa-4,13-dioxo-5,12-diazahexadecane 1,16-dioxydi(meth)acrylate (UDMA),
         alkoxylated bisphenol A di(meth)acrylates having 2 to 6 alkoxy units,
         poly(meth)acrylates containing hydroxyl groups, selected from the group consisting of dipentaerythritol di(meth)acrylate, alkoxylated dipentaerythritol di(meth)acrylate, dipentaerythritol tri(meth)acrylate, alkoxylated dipentaerythritol tri(meth)acrylate, dipentaerythritol tetra(meth)acrylate, alkoxylated dipentaerythritol tetra(meth)acrylate, dipentaerythritol penta(meth)acrylate, alkoxylated dipentaerythritol penta(meth)acrylate, pentaerythritol di(meth)acrylate, alkoxylated pentaerythritol di(meth)acrylate, pentaerythritol tri(meth)acrylate, alkoxylated pentaerythritol tri(meth)acrylate,
      and
         light-curable, chain-like and/or cyclic and/or cage-type polysiloxanes,
   (A2) 40% to 90% by weight, preferably 50% to 80% by weight, more preferably 60% to 75% by weight, of 2,2-bis[4-(2-hydroxy-3-methacryloyloxypropoxy)phenyl]propane (bis-GMA) and/or light-curable derivatives of diisocyanatodiphenylmethane (MDI) and/or light-curable derivatives of tetramethyl-m-xylylene diisocyanate (TMXDI),
   (A5) 0% to 15% by weight, preferably 0% to 10% by weight, more preferably 0% to 5% by weight, most preferably 0% by weight, of further free-radically polymerizable monomers that cannot be assigned to (A4) or (A2),
   wherein the percentages by weight of (A4), (A2) and (A5) are based on the total mass of the monomers (A).

13. Dental, light-curable, one-component composite composition according to any of Aspects 1-6, wherein the monomers (A) consist of
   (A4) 10% to 60% by weight, preferably 20% to 50% by weight, more preferably 25% to 40% by weight, of one or more compounds selected from the group consisting of
      light-curable bi- or tricyclic compounds $Q(Y_xZ_e)_b$ wherein
      Q denotes a saturated or olefinically unsaturated bi- or tricyclic structural element,
      each index b is a natural number selected from the group of the natural numbers 1, 2, and 3,
      each Z denotes a light-curable group,
      each index e is a natural number selected from the group of the natural numbers 1, 2 and 3,
      each Y in the structure $Q(Y_xZ_e)_b$ with x=1 denotes a structural element which connects the structural element Q to e structural elements Z and which denotes a straight or branched alkylene group, wherein the alkylene group may be interrupted by oxygen atoms, and
      each index x is 0 or 1,
         7,7,9-trimethyl-3,14-dioxa-4,13-dioxo-5,12-diazahexadecane 1,16-dioxydi(meth)acrylate (UDMA),
         7,9,9-trimethyl-3,14-dioxa-4,13-dioxo-5,12-diazahexadecane 1,16-dioxydi(meth)acrylate
         7,9-dimethyl-3,14-dioxa-4,13-dioxo-5,12-diazahexadecane 1,16-dioxydi(meth)acrylate
         3,14-dioxa-4,13-dioxo-5,12-diazahexadecane 1,16-dioxydi(meth)acrylate
         1,5,5-trimethyl-1-[(2-methacryloyloxyethyl)carbamoylmethyl]-3-(2-methacryloyloxyethyl)carbamoylcyclohexane
         7,7,9,9-tetramethyl-3,14-dioxa-4,13-dioxo-5,12-diazahexadecane 1,16-dioxydi(meth)acrylate
         2,7,7,9,15-pentamethyl-3,14-dioxa-4,13-dioxo-5,12-diazahexadecane 1,16-dioxydi(meth)acrylate
         2,7,9,9,15-pentamethyl-3,14-dioxa-4,13-dioxo-5,12-diazahexadecane 1,16-dioxydi(meth)acrylate
         2,7,9,15-tetramethyl-3,14-dioxa-4,13-dioxo-5,12-diazahexadecane 1,16-dioxydi(meth)acrylate
         2,15-dimethyl-3,14-dioxa-4,13-dioxo-5,12-diazahexadecane 1,16-dioxydi(meth)acrylate
         1,5,5-trimethyl-1-[(1-methacryloyloxypropan-2-yl)carbamoylmethyl]-3-(1-methacryloyloxypropan-2-yl)carbamoylcyclohexane
         2,7,7,9,9,15-hexamethyl-3,14-dioxa-4,13-dioxo-5,12-diazahexadecane 1,16-dioxydi(meth)acrylate,
         alkoxylated bisphenol A di(meth)acrylates having 2 to 6 alkoxy units,
         poly(meth)acrylates containing hydroxyl groups, selected from the group consisting of dipentaerythritol di(meth)acrylate, alkoxylated dipentaerythritol di(meth)acrylate, dipentaerythritol tri(meth)acrylate, alkoxylated dipentaerythritol tri(meth)acrylate, dipentaerythritol tetra(meth)acrylate, alkoxylated dipentaerythritol tetra(meth)acrylate, dipentaerythritol penta(meth)acrylate, alkoxylated dipentaerythritol penta(meth)acrylate, pentaerythritol di(meth)acrylate, alkoxylated pentaerythritol di(meth)acrylate, pentaerythritol tri(meth)acrylate, alkoxylated pentaerythritol tri(meth)acrylate, and light-curable, chain-like and/or cyclic and/or cage-type polysiloxanes, (A2) 40% to 90% by weight, preferably 50% to 80% by weight, more preferably 60% to 75% by weight, of 2,2-bis[4-(2-hydroxy-3-methacryloyloxypropoxy)phenyl]propane (bis-GMA) and/or light-curable derivatives of diisocyanatodiphenylmethane (MDI) and/or light-curable derivatives of tetramethyl-m-xylylene diisocyanate (TMXDI), (A5) 0% to 15% by weight, preferably 0% to 10% by weight, more preferably 0% to 5% by weight, most preferably 0% by weight, of further free-radically polymerizable monomers that cannot be assigned to (A4) or (A2), wherein the percentages by weight of (A4), (A2) and (A5) are based on the total mass of the monomers (A).

14. Dental, light-curable, one-component composite composition according to any of Aspects 1 to 5, wherein component (A) comprises more than 60% by weight of light-curable, chain-like and/or cyclic and/or cage-type polysiloxanes.

15. Dental, light-curable, one-component composite composition according to any of the preceding aspects, wherein the fillers (B) consist of and/or are producible by mixing (B1) 2% to 25% by weight, preferably 3% to 20% by weight, of inorganic filler having a $D_{50}$ of 1 nm to 200 nm, and further filler constituents, preferably (B2) 40% to 90% by weight, preferably 50% to 80% by weight, of inorganic filler having a $D_{50}$ of greater than 1 μm to 10 μm, (B3) 8% to 50% by weight, preferably 15% to 40% by weight, of inorganic filler in a size having a $D_{50}$ of 0.4 μm to 1.0 μm and (B4) 0% to 25% by weight, preferably 0% to 15% by weight, of further fillers that cannot be assigned to (B1), (B2) or (B3), wherein the percentages by weight of (B1), (B2), (B3) and (B4) are based on the total mass of the fillers (B).

16. Dental, light-curable, one-component composite composition according to Aspect 15, wherein the particles of the inorganic filler (B1) are not aggregated and not agglomerated and/or the inorganic filler (B1) is in a size having a $D_{50}$ below 100 nm, preferably below 70 nm, and/or the inorganic filler (B2) is in a size having a $D_{50}$ of 1.2 μm to 5.0 μm, preferably of 1.5 μm to 4.0 μm, and/or the inorganic filler (B3) is in a size having a $D_{50}$ of 0.5 μm to 0.9 μm and preferably of 0.6 μm to 0.8 μm.

17. Dental, light-curable, one-component composite composition according to any of Aspects 15 or 16, wherein (B1) contains oxides or mixed oxides selected from the group consisting of the elements silicon, titanium, yttrium, barium, zirconium, hafnium, niobium, tantalum, tungsten, bismuth, molybdenum, tin, zinc, ytterbium, lanthanum, cerium, aluminium and mixtures thereof, preferably silica, and/or sulfides, selenides and tellurides of metals, mixed metals and mixtures thereof and/or salts of the rare earths, of scandium and of yttrium, preferably ytterbium fluoride, and/or salts of barium and of strontium, preferably barium sulfate and/or strontium fluoride, and/or mixed fluorides between ytterbium fluoride and strontium fluoride, preferably strontium fluoride-doped ytterbium fluoride and/or ytterbium fluoride-doped strontium fluoride.

18. Dental, light-curable, one-component composite composition according to any of Aspects 15 to 17, wherein constituents (B2) and (B3) comprise:

materials based on oxides or mixed oxides of $SiO_2$, $ZrO_2$, $TiO_2$ and/or quartz glass ceramic or glass powder, barium silicate glasses, barium fluorosilicate glasses, strontium silicate glasses, strontium borosilicates, Li/Al silicate glasses, barium glasses, calcium silicates, sodium aluminium silicates, fluoroaluminium silicate glasses, oxides of aluminium or silicon, zeolites, apatite, zirconium silicates and/or metal salts, preferably barium sulfate or calcium fluoride, and/or ytterbium fluoride.

19. Dental, light-curable, one-component composite composition according to any of Aspects 15 to 18, wherein the ratio of the total mass of (B2) to (B3) is in the range from 1:1 to 12:1, preferably in the range from 1.5:1 to 8:1 and/or wherein the ratio of the average particle size of (B2) to the average particle size of (B3) is in the range from 1.5:1 to 10:1, preferably in the range from 2:1 to 5:1.

20. Dental, light-curable, one-component composite composition according to any of Aspects 15 to 19, wherein (B4) comprises reinforcing filler materials, preferably glass fibres or polyamide or carbon fibres and/or further inorganic fillers and/or splinter or bead polymers, preferably bead polymers of homo- or copolymers of organically curable monomers.

21. Dental, light-curable, one-component composite composition according to any of Aspects 15 to 20, wherein components (B1) and/or (B2) and/or (B3) and/or (B4) have been organically surface-modified, preferably silanized.

22. Dental, light-curable, one-component composite composition according to any of Aspects 15 to 21, wherein components (B1) and/or (B2) and/or (B3) and/or (B4) have been surface-modified by compounds of the general formula X-Sp-V wherein "X" and "V" denote functional groups connected to one another by a linker "Sp" and wherein the functional group "X" is selected such that it can enter into a corresponding bond to the surface of the filler particle with complex formation, and is preferably a group of the silane, phosphate, phosphonate, carboxylate, dithiophosphate, dithiophosphonate, amine or amide type, and the linker "Sp" has linear or branched alkyl chains, aromatic systems or combinations of these groups, each of which may be interrupted by heteroatoms such as O, N, or P or by a urethane group and the functional group "V" has light-curable groups, preferably (meth)acrylate groups.

23. Dental, light-curable, one-component composite composition according to any of Aspects 15 to 22, wherein components (B1) and/or (B2) and/or (B3) and/or (B4) have been silanized with a compound of the formula (1) or (2)

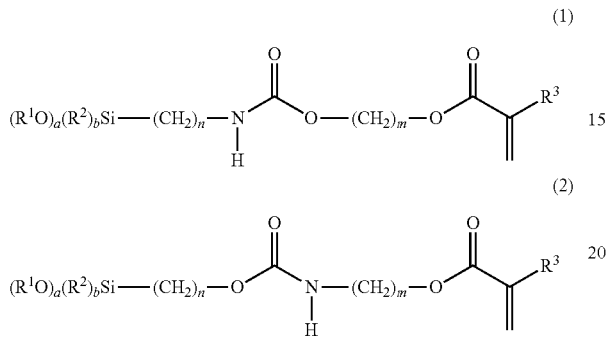

wherein $R^1$ denotes a C1- to C4-alkyl group, and
$R^2$ denotes a C1- to C8-alkyl group, and
$R^3$ denotes a hydrogen atom or a methyl group, and
a=1, 2 or 3, and
b=3−a, and
n=1 to 8, and
m=1 to 8.

24. Cured composite composition, obtained by light curing of a dental, light-curable, one-component composite composition according to any of the preceding aspects.

25. Dental, light-curable, one-component composite composition according to any of Aspects 1 to 23, for use in a method of dental treatment,
preferably for use in a method of dental treatment having the following steps:
heating the composite composition to a temperature of 40° C. or more, preferably a temperature in the range from 40° C. to 80° C., preferably in an oven and/or by irradiation, preferably with IR rays,
contacting the composite composition that has been heated to a temperature of 40° C. or more, preferably a temperature in the range from 40° C. to 80° C., with a patient's tooth to be treated, preferably as dental filling material, lining material, luting material and fissure sealant.

26. Use of a composite composition according to any of Aspects 1 to 23 for production of a dental product, wherein the production is not effected on the human or animal body.

27. Device for applying a composite composition, comprising
a cavity filled at least partly with an amount of a composite composition according to any of Aspects 1 to 23 and
an application tip connected to the cavity and having an exit opening for the composite composition.

28. Device according to Aspect 27, wherein the exit opening has a cross-sectional exit area in the range from 0.2 to 3.0 mm$^2$, preferably a cross-sectional exit area of not more than 2.0 mm$^2$, more preferably a cross-sectional exit area of not more than 1.5 mm$^2$.

29. Device according to any of Aspects 27 or 28, wherein the application tip is a cannula preferably consisting of metal or plastic
and/or
the device is selected from the group consisting of compules and syringes.

30. Method of producing a composite composition according to any of Aspects 1 to 23 or for producing a device for application of a composite composition according to any of Aspects 27 to 29, having the following step:
mixing the constituents
(A) monomers in an amount of 6% to 35% by weight, based on the total amount of the composite composition, preferably 10% to 35% by weight, more preferably 10% to 25% by weight,
(B) fillers in an amount of 65% to 93% by weight, preferably 65% to 89% by weight, more preferably 75% to 89% by weight, based on the total amount of the composite composition,
(C) initiators in an amount of 0.001% to 3% by weight based on the total amount of the composite composition,
(D) further additives in an amount of 0.001% to 5% by weight based on the total amount of the composite composition,
to give the composite composition,
wherein the constituents are selected such that the viscosity $\eta_{20}$ of the composite composition at 20° C. is greater than 400 Pa*s and the viscosity $\eta_{50}$ of the composite composition at 50° C. is less than 150 Pa*s and wherein the quotient $\eta_{50}/\eta_{20}$ of the viscosity of the composite composition at 50° C. and the viscosity of the composite composition at 20° C. is less than 0.125, preferably less than 0.1.

31. Method according to Aspect 30, wherein
constituent (A) is produced by the following steps:
providing at least
(A-i) one first monomer substance and
(A-ii) one second monomer substance,
wherein
the viscosity $\eta_{20}$ of the second monomer substance (A-ii) at 20° C. is greater than 100 Pa*s,
the viscosity $\eta_{20}$ of the first monomer substance (A-i) at 20° C. is greater than 100 mPa*s,
the viscosity of the second monomer substance (A-ii) at 20° C. is greater than that of the first monomer substance (A-i) and
the mass ratio of the first monomer substance (A-i) to the second monomer substance (A-ii) is in the range from 2:1 to 1:10,
wherein the second monomer substance (A-ii) preferably contains at least 40% by weight of 2,2-bis[4-(2-hydroxy-3-methacryloyloxypropoxy)phenyl]propane (bis-GMA) and/or light-curable derivatives of diisocyanatodiphenylmethane (MDI) and/or light-curable derivatives of tetramethyl-m-xylylene diisocyanate (TMXDI), where the percentage by weight is based on the total mass of the monomers (A), and
mixing the monomer substances (A-i) and (A-ii) provided, prior to the and/or in the course of mixing with constituents (B), (C) and (D),
and/or wherein
constituent (B) is produced by mixing
(B1) 2% to 25% by weight, preferably 3% to 20% by weight, of inorganic filler having a $D_{50}$ of 1 nm to 200 nm, and further filler constituents, preferably (B2) 40% to 90% by weight, preferably 50% to 80% by weight, of inorganic filler having a $D_{50}$ of greater than 1 μm to 10 μm, (B3) 8% to 50% by weight, preferably 15% to 40% by weight, of inorganic filler in a size having a $D_{50}$ of 0.4 μm to 1.0 μm and (B4) 0% to 25% by weight, preferably 0% to 15% by weight, of further fillers that cannot be assigned to (B1), (B2) or (B3), wherein the percentages by weight of (B1), (B2), (B3) and (B4) are based on the total mass of the fillers (B).

32. Method according to either of Aspects 30 and 31, having the following additional step for preparation of the device for application of a composite composition:

introducing the composition according to any of Aspects 1 to 23 that has been produced into a cavity of a previously unfilled device for application of a composite composition.

33. Method of preparing for a dental treatment of a patient, having the following step: heating a composite composition according to any of Aspects 1 to 23 or a device according to any of Aspects 27 to 29, preferably produced by a method according to Aspect 30 to 32, to a temperature of 40° C. or more, preferably a temperature in the range from 40° C. to 80° C., preferably in an oven and/or by irradiation, preferably with IR rays.

34. Use of a dental, light-curable, one-component composite composition according to any of Aspects 1 to 23 in a method of dental treatment, preferably for use in a method of dental treatment having the following steps:

heating the composite composition to a temperature of 40° C. or more, preferably a temperature in the range from 40° C. to 80° C., preferably in an oven and/or by irradiation, preferably with IR rays, contacting the composite composition that has been heated to a temperature of 40° C. or more, preferably a temperature in the range from 40° C. to 80° C., with a patient's tooth to be treated, preferably as dental filling material, lining material, luting material and fissure sealant.

The invention claimed is:

1. Dental, light-curable, one-component composite composition, comprising:
(A) monomers,
(B) fillers, and
(C) initiators,
wherein:
the viscosity $\eta_{20}$ of the composite composition at 20° C. is greater than 400 Pa*s and
the viscosity $\eta_{50}$ of the composite composition at 50° C. is less than 150 Pa*s and
the quotient $\eta_{50}/\eta_{20}$ of the viscosity of the composite composition at 50° C. and the viscosity of the composite composition at 20° C. is less than 0.125, and wherein the (A) monomers consist of:
(A1) 10% to 60% by weight, of light-curable bi- or tricyclic compounds $Q(Y_xZ_e)_b$ wherein
Q denotes a saturated or olefinically unsaturated bi- or tricyclic structural element,
each index b is a natural number selected from the group of the natural numbers 1, 2, and 3,
each Z denotes a light-curable group,
each index e is a natural number selected from the group of the natural numbers 1, 2 and 3,
each Y in the structure $Q(Y_xZ_e)_b$ with x=1 denotes a structural element which connects the structural element Q to e structural elements Z and which denotes a straight or branched alkylene group, wherein the alkylene group may be interrupted by oxygen atoms, and each index x is 0 or 1, (A2) 40% to 90% by weight, of 2,2-bis[4-(2-hydroxy-3-methacryloyloxypropoxy)phenyl]propane (bis-GMA) and/or light-curable derivatives of diisocyanatodiphenylmethane (MDI) and/or light-curable derivatives of tetramethyl-m-xylylene diisocyanate (TMXDI), and (A3) 0% to 15% by weight, of further free-radically polymerizable monomers that cannot be assigned to (A1) or (A2), wherein the percentages by weight (A1), (A2) and (A3) are based on the total mass of the monomers (A).

2. Dental, light-curable, one-component composite composition according to claim 1, wherein
the viscosity $\eta_{20}$ of the composite composition at 20° C. is greater than 800 Pa*s, and/or
the viscosity $\eta_{50}$ of the composite composition at 50° C. is less than 120 Pa*s, and/or
the quotient $\eta_{50}/\eta_{20}$ of the viscosity of the composite composition at 50° C. and the viscosity of the composite composition at 20° C. is less than 0.1.

3. Dental, light-curable, one-component composite composition according to claim 1, wherein the viscosity l37 of the composite composition at 37° C. is greater than 400 Pa*s.

4. Dental, light-curable, one-component composite composition according to claim 1, selected from the group consisting of dental filling material, lining material, luting material and fissure sealant.

5. Dental, light-curable, one-component composite composition according to claim 1, comprising:
(A) monomers in an amount of 6% to 35% by weight, based on the total amount of the composite composition,
(B) fillers in an amount of 65% to 93% by weight, based on the total amount of the composite composition,
(C) initiators in an amount of 0.001% to 3% by weight, based on the total amount of the composite composition,
(D) further additives in an amount of 0.001% to 5% by weight, based on the total amount of the composite composition.

6. Dental, light-curable, one-component composite composition according to claim 1, wherein Q is selected from the group of structural elements consisting of
bicyclo[1.1.1]pentane, bicyclo[2.1.1]hexane, bicyclo[2.2.1]heptane, bicyclo[2.2.1]heptene, bicyclo[3.1.1]heptane, bicyclo[2.2.2] octane, bicyclo[4.1.1]octane, bicyclo[3.2.1] octane, bicyclo[4.2.1]nonane, bicyclo[3.3.1]nonane, bicyclo[5.1.1]nonane, bicyclo[3.2.2]nonane, bicyclo[6.1.1]decane, bicyclo[5.2.1]decane, bicyclo[4.2.2]decane, bicyclo[3.3.2]decane, bicyclo[7.1.1]undecane, bicyclo[6.2.1]undecane, bicyclo[5.2.2]undecane, bicyclo[4.3.2]undecane, bicyclo[3.3.3]undecane, bicyclo[8.1.1]dodecane, bicyclo[7.2.1]dodecane, bicyclo[6.2.2]dodecane, bicyclo[5.3.2] dodecane, bicyclo[4.3.3]dodecane, bicyclo[4.4.2]dodecane, bicyclo[5.4.1]dodecane, bicyclic tridecanes, bicyclic tetradecanes, bicyclic pentadecanes,
tricyclo[3.2.1.0$^{2,6}$]octane, tricyclo[4.2.1.0$^{2,6}$]nonane, tricyclo[5.2.1.0$^{2,6}$] decane, tricyclo[6.2.1.0$^{2,6}$]undecane, tricyclo[7.2.1.0$^{2,6}$]dodecane, tricyclo[4.2.1.1$^{2,5}$]decane, tricyclo[4.3.1.1$^{2,5}$]decane, tricyclo[4.4.1.1$^{2,5}$]decane, tricyclo[2.2.1.0$^{2,6}$]heptane, tricyclo[2.2.2.0$^{2,6}$]octane, tricyclo[3.2.2.0$^{2,6}$]nonane, tricyclo[3.3.1.1$^{3,7}$]decane, tricyclo[3.2.1.1$^{3,7}$]nonane, tricyclo[4.2.2.2$^{2,5}$]dodecane, tricyclo[4.3.2.2$^{2,5}$]tridecane, tricyclo[4.4.2.2$^{2,5}$]tetradecane, tricyclo[4.2.1.0$^{3,7}$]nonane, tricyclo[4.4.1.1$^{1,5}$]dodecane, tricyclo[6.2.1.0$^{2,7}$]undecane, tricyclo[5.2.2.0$^{2,6}$]undecane, tricyclo[6.2.2.0$^{2,7}$]dodecane, tricyclo[4.3.2.0$^{2,5}$]undecane, tricyclo[4.2.2.0$^{2,5}$]decane and tricyclo[5.5.1.0$^{3,11}$]tridecane.

7. Dental, light-curable, one-component composite composition according to claim 1, wherein the light-curable group Z denotes a structural element selected from the group consisting of —O—(C=O)—CH=CH$_2$, —O—(C=O)—C(CH$_3$)=CH$_2$, —(C=O)—CH=CH$_2$, —(C=O)—C(CH$_3$)=CH$_2$, —CH=CH$_2$, —C(CH$_3$)=CH$_2$, —CH$_2$—CH=CH$_2$, —CH$_2$—C(CH$_3$)=CH$_2$ and —O—CH=CH$_2$.

8. Dental, light-curable, one-component composite composition according to claim 1, wherein component (A1) is bis(methacryloyloxymethyl)tricyclo[5.2.1.0$^{2,6}$]decane and/or alkoxylated bis(methacryloyloxymethyl)tricyclo[5.2.1.0$^{2,6}$]decane, and/or component (A2) is bis-GMA.

9. Dental, light-curable, one-component composite composition according to claim 1, wherein (A3) is selected from the group consisting of ethylene glycol di(meth)acrylate, alkoxylated ethylene glycol di(meth)acrylate, diethylene glycol di(meth)acrylate, hexane-1,6-diol di(meth)acrylate, triethylene glycol di(meth)acrylate, dodecane-1,12-diol di(meth)acrylate, decane-1,10-diol di(meth)acrylate, bisphenol A di(meth)acrylate, alkoxylated bisphenol A di(meth)acrylate, polyethylene glycol di(meth)acrylate, propylene glycol di(meth)acrylate, dipropylene glycol di-(meth)acrylate, tripropylene glycol di(meth)acrylate, tetrapropylene glycol di(meth)acrylate, polypropylene glycol di(meth)acrylate, 7,7,9-trimethyl-3,14-dioxa-4,13-dioxo-5,12-diazahexadecane 1,16-dioxydi(meth)acrylate, butanediol di(meth)acrylate, propanediol di(meth)acrylate, tetraethylene glycol di(meth)acrylate, neopentyl glycol di(meth)acrylate, alkoxylated neopentyl glycol di(meth)acrylate, 2-hydroxypropyl 1,3-di(meth)acrylate, 3-hydroxypropyl 1,2-di(meth)acrylate, pentaerythritol di(meth)acrylate, alkoxylated pentaerythritol di(meth)acrylate, pentaerythritol tri(meth)acrylate, alkoxylated pentaerythritol tri(meth)acrylate, pentaerythritol tetra(meth)acrylate, alkoxylated pentaerythritol tetra(meth)acrylate, dipentaerythritol di(meth)acrylate, alkoxylated dipentaerythritol di(meth)acrylate, dipentaerythritol tri(meth)acrylate, alkoxylated dipentaerythritol tri(meth)acrylate, dipentaerythritol tetra(meth)acrylate, alkoxylated dipentaerythritol tetra(meth)acrylate, dipentaerythritol penta(meth)acrylate, alkoxylated dipentaerythritol penta(meth)acrylate, dipentaerythritol hexa(meth)acrylate, alkoxylated dipentaerythritol hexa(meth)acrylate, trimethylolpropane tri(meth)acrylate, alkoxylated trimethylolpropane tri(meth)acrylate and cyclohexanedimethanol di(meth)acrylate.

10. Dental, light-curable, one-component composite composition according to claim 1, wherein
the fillers (B) are producible by mixing
(B1) 2% to 25% by weight of inorganic filler having a $D_{50}$ of 1 nm to 200 nm,
and further filler constituents,
(B2) 40% to 90% by weight of inorganic filler having a $D_{50}$ of greater than 1 μm to 10 μm,
(B3) 8% to 50% by weight of inorganic filler in a size having a $D_{50}$ of 0.4 μm to 1.0 μm, and
(B4) 0% to 25% by weight of further fillers that cannot be assigned to (B1), (B2) or (B3),
wherein the percentages by weight of (B1), (B2), (B3) and (B4) are based on the total mass of the fillers (B).

11. Dental, light-curable, one-component composite composition according to claim 10, wherein
the particles of the inorganic filler (B1) are not aggregated and not agglomerated and/or
the inorganic filler (B1) is in a size having a $D_{50}$ below 100 nm,
and/or
the inorganic filler (B2) is in a size having a $D_{50}$ of 1.2 μm to 5.0 μm,
and/or
the inorganic filler (B3) is in a size having a $D_{50}$ of 0.5 μm to 0.9 μm.

12. Dental, light-curable, one-component composite composition according to claim 10, wherein (B1) contains
oxides or mixed oxides selected from the group consisting of the elements silicon, titanium, yttrium, barium, zirconium, hafnium, niobium, tantalum, tungsten, bismuth, molybdenum, tin, zinc, ytterbium, lanthanum, cerium, aluminium and mixtures thereof, and/or
sulfides, selenides and tellurides of metals, mixed metals and mixtures thereof and/or
salts of the rare earths, of scandium and of yttrium, and/or
salts of barium and of strontium, and/or
mixed fluorides between ytterbium fluoride and strontium fluoride.

13. Dental, light-curable, one-component composite composition according to claim 10, wherein constituents (B2) and (B3) comprise:
materials based on oxides or mixed oxides of $SiO_2$, $ZrO_2$, $TiO_2$ and/or
quartz glass ceramic or glass powder, barium silicate glasses, barium fluorosilicate glasses, strontium silicate glasses, strontium borosilicates, Li/Al silicate glasses, barium glasses, calcium silicates, sodium aluminium silicates, fluoroaluminium silicate glasses, oxides of aluminium or silicon, zeolites, apatite, zirconium silicates and/or
metal salts, and/or
ytterbium fluoride.

14. Dental, light-curable, one-component composite composition according to claim 10,
wherein the ratio of the total mass of (B2) to (B3) is in the range from 1:1 to 12:1, and/or
wherein the ratio of the average particle size of (B2) to the average particle size of (B3) is in the range from 1.5:1 to 10:1.

15. Dental, light-curable, one-component composite composition according to claim 10, wherein (B4) comprises
reinforcing filler materials,
and/or
further inorganic fillers
and/or
splinter or bead polymers.

16. Dental, light-curable, one-component composite composition according to claim 10,
wherein components (B1) and/or (B2) and/or (B3) and/or (B4) have been organically surface-modified.

17. Dental, light-curable, one-component composite composition according to claim 10, wherein components (B1) and/or (B2) and/or (B3) and/or (B4) have been surface-modified by compounds of the general formula X-Sp-V
wherein "X" and "V" denote functional groups connected to one another by a linker "Sp" and wherein the functional group "X" is selected such that it can enter into a corresponding bond to the surface of the filler particle with complex formation, and the linker "Sp" has linear or branched alkyl chains, aromatic systems or combinations of these groups, each of which may be interrupted by heteroatoms such as O, N, or P or by a urethane group and the functional group "V" has light-curable groups.

18. Dental, light-curable, one-component composite composition according to claim 10, wherein components (B1) and/or (B2) and/or (B3) and/or (B4) have been silanized with a compound of the formula (1) or (2)

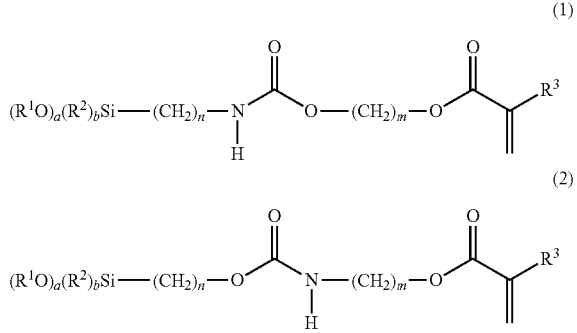

wherein $R^1$ denotes a C1- to C4-alkyl group, and
$R^2$ denotes a C1- to C8-alkyl group, and
$R^3$ denotes a hydrogen atom or a methyl group, and
a=1, 2 or 3, and
b=3−a, and
n=1 to 8, and
m=1 to 8.

19. Cured composite composition, obtained by light curing of a dental, light-curable, one-component composite composition according to claim 1.

20. Dental, light-curable, one-component composite composition according to claim 1, for use in a method of dental treatment having the following steps:
heating the composite composition to a temperature of 40° C. or more,
contacting the composite composition that has been heated to a temperature of 40° C. or more with a patient's tooth to be treated.

21. A method for production of a dental product, wherein the production is not effected on the human or animal body, the method comprising:
curing a dental, light-curable, one-component composite composition according to claim 1.

22. Device for applying a composite composition, comprising
a cavity filled at least partly with an amount of a composite composition according to claim 1 and
an application tip connected to the cavity and having an exit opening for the composite composition.

23. Device according to claim 22, wherein the exit opening has a cross-sectional exit area in the range from 0.2 to 3.0 $mm^2$.

24. Device according to claim 22, wherein
the application tip is a cannula
and/or
the device is selected from the group consisting of compules and syringes.

25. Method of producing a composite composition according to claim 1 having the following step:
(A) monomers in an amount of 6% to 35% by weight, based on the total amount of the composite composition,
(B) fillers in an amount of 65% to 93% by weight based on the total amount of the composite composition,
(C) initiators in an amount of 0.001% to 3% by weight based on the total amount of the composite composition,
(D) further additives in an amount of 0.001% to 5% by weight based on the total amount of the composite composition,
to give the composite composition,
wherein the constituents are selected such that the viscosity $\eta_{20}$ of the composite composition at is greater than 400 Pa*s and the viscosity $\eta_{50}$ of the composite composition at 50° C. is less than 150 Pa*s and wherein the quotient $\eta_{50}/\eta_{20}$ of the viscosity of the composite composition at and the viscosity of the composite composition at 20° C. is less than 0.125.

26. Method according to claim 25, having the following additional step for preparation of the device for application of a composite composition:
introducing the composite composition that has been produced into a cavity of a previously unfilled device for application of a composite composition.

27. Method of preparing for a dental treatment of a patient, having the following step:
heating a composite composition according to claim 1 or a device, to a temperature of 40° C. or more in an oven and/or by irradiation,
wherein the device comprises a cavity filled at least partly with an amount of the composite composition and an application tip connected to the cavity and having an exit opening for the composite composition.

* * * * *

UNITED STATES PATENT AND TRADEMARK OFFICE
CERTIFICATE OF CORRECTION

PATENT NO. : 11,944,692 B2
APPLICATION NO. : 17/252588
DATED : April 2, 2024
INVENTOR(S) : Christoph Hahn et al.

It is certified that error appears in the above-identified patent and that said Letters Patent is hereby corrected as shown below:

In the Claims

In Column 54, Line 28 of Claim 3 reads "position according to claim 1, wherein the viscosity 137 of" but should read -- position according to claim 1, wherein the viscosity η37 of --

Signed and Sealed this
Third Day of September, 2024

Katherine Kelly Vidal
*Director of the United States Patent and Trademark Office*